US011224425B2

(12) United States Patent
Schings

(10) Patent No.: US 11,224,425 B2
(45) Date of Patent: Jan. 18, 2022

(54) SURGICAL LINEAR CUTTER WISHBONE SEPARATION MECHANISM WITH DETENT

(71) Applicant: Ethicon LLC, Guaynabo, PR (US)

(72) Inventor: Brian D. Schings, Cincinnati, OH (US)

(73) Assignee: Cilag GmbH International, Zug (CH)

(*) Notice: Subject to any disclaimer, the term of this patent is extended or adjusted under 35 U.S.C. 154(b) by 27 days.

(21) Appl. No.: 16/886,919

(22) Filed: May 29, 2020

(65) Prior Publication Data

US 2021/0369270 A1 Dec. 2, 2021

(51) Int. Cl.
*A61B 17/072* (2006.01)
*A61B 17/11* (2006.01)
(Continued)

(52) U.S. Cl.
CPC ...... *A61B 17/072* (2013.01); *A61B 17/07207* (2013.01); *A61B 17/115* (2013.01); *A61B 17/1114* (2013.01); *A61B 17/068* (2013.01); *A61B 2017/00367* (2013.01); *A61B 2017/00477* (2013.01); *A61B 2017/07214* (2013.01); *A61B 2017/07264* (2013.01); *A61B 2017/07271* (2013.01); *A61B 2017/07285* (2013.01); *A61B 2017/2927* (2013.01); *A61B 2017/2946* (2013.01)

(58) Field of Classification Search
CPC ............... A61B 17/072; A61B 17/068; A61B 17/07207; A61B 17/1114; A61B 17/115; A61B 2017/00477; A61B 2017/07214; A61B 2017/07271; A61B 2017/2927; A61B 2017/2946; A61B 2017/00473; A61B 2017/07285

USPC .............. 227/19, 175.2, 175.3, 176.1, 180.1; 606/1, 139, 219
See application file for complete search history.

(56) References Cited

U.S. PATENT DOCUMENTS 4,608,981 A * 9/1986 Rothfuss .......... A61B 17/07207
227/180.1
5,718,359 A * 2/1998 Palmer ............ A61B 17/07207
227/175.2
(Continued)

OTHER PUBLICATIONS

U.S. Appl. No. 16/886,920, entitled "Pin Trap Mechanism for Surgical Linear Cutter," filed May 29, 2020.
(Continued)

*Primary Examiner* — Scott A Smith
(74) *Attorney, Agent, or Firm* — Frost Brown Todd LLC

(57) ABSTRACT

A surgical stapler includes a first half having a first elongate member and a surface with staple forming pockets. The stapler also includes a second half for releasably coupling with the first half and including a second elongate member having a distal portion for deploying staples. The elongate members are pivotable relative to each other about a pivot axis when the halves are releasably coupled. The stapler further includes a latching member for selectively clamping the halves in a clamped state. The stapler also includes a detent member extending laterally from one of the halves toward the other. The stapler further includes a shoulder member positioned on the other of the halves and configured to selectively engage the detent member in response to rotation of the first elongate member away from the second elongate member to an open state in which the elongate members assume a maximum angular orientation.

20 Claims, 23 Drawing Sheets

(51) Int. Cl.
*A61B 17/115* (2006.01)
*A61B 17/00* (2006.01)
*A61B 17/068* (2006.01)
*A61B 17/29* (2006.01)

(56) References Cited

U.S. PATENT DOCUMENTS

| | | | | |
|---|---|---|---|---|
| 5,878,938 | A * | 3/1999 | Bittner | A61B 17/07207 |
| | | | | 227/175.4 |
| 7,334,717 | B2 * | 2/2008 | Rethy | A61B 17/105 |
| | | | | 227/175.1 |
| 7,832,612 | B2 * | 11/2010 | Baxter, III | A61B 17/068 |
| | | | | 227/175.2 |
| 8,505,801 | B2 * | 8/2013 | Ehrenfels | A61B 17/105 |
| | | | | 227/175.2 |
| 9,402,629 | B2 | 8/2016 | Ehrenfels et al. | |
| 10,631,866 | B2 | 4/2020 | Laurent et al. | |
| 10,898,187 | B2 | 1/2021 | Deck et al. | |
| 2019/0239882 | A1 | 8/2019 | McLain et al. | |
| 2019/0239883 | A1 | 8/2019 | Baxter, III et al. | |
| 2019/0239884 | A1 | 8/2019 | Baxter, III et al. | |
| 2019/0239885 | A1 | 8/2019 | Stokes et al. | |
| 2019/0239886 | A1 | 8/2019 | Jones et al. | |
| 2020/0046350 | A1 | 2/2020 | Deck et al. | |
| 2020/0046351 | A1 | 2/2020 | Jones et al. | |
| 2020/0046353 | A1 | 2/2020 | Deck et al. | |
| 2020/0113561 | A1 | 4/2020 | Schings et al. | |
| 2020/0113562 | A1 | 4/2020 | Schings et al. | |
| 2021/0038223 | A1 | 2/2021 | Schings et al. | |

OTHER PUBLICATIONS

U.S. Appl. No. 16/886,924, entitled "Separation Mechanism for Surgical Linear Cutter," filed May 29, 2020.

* cited by examiner

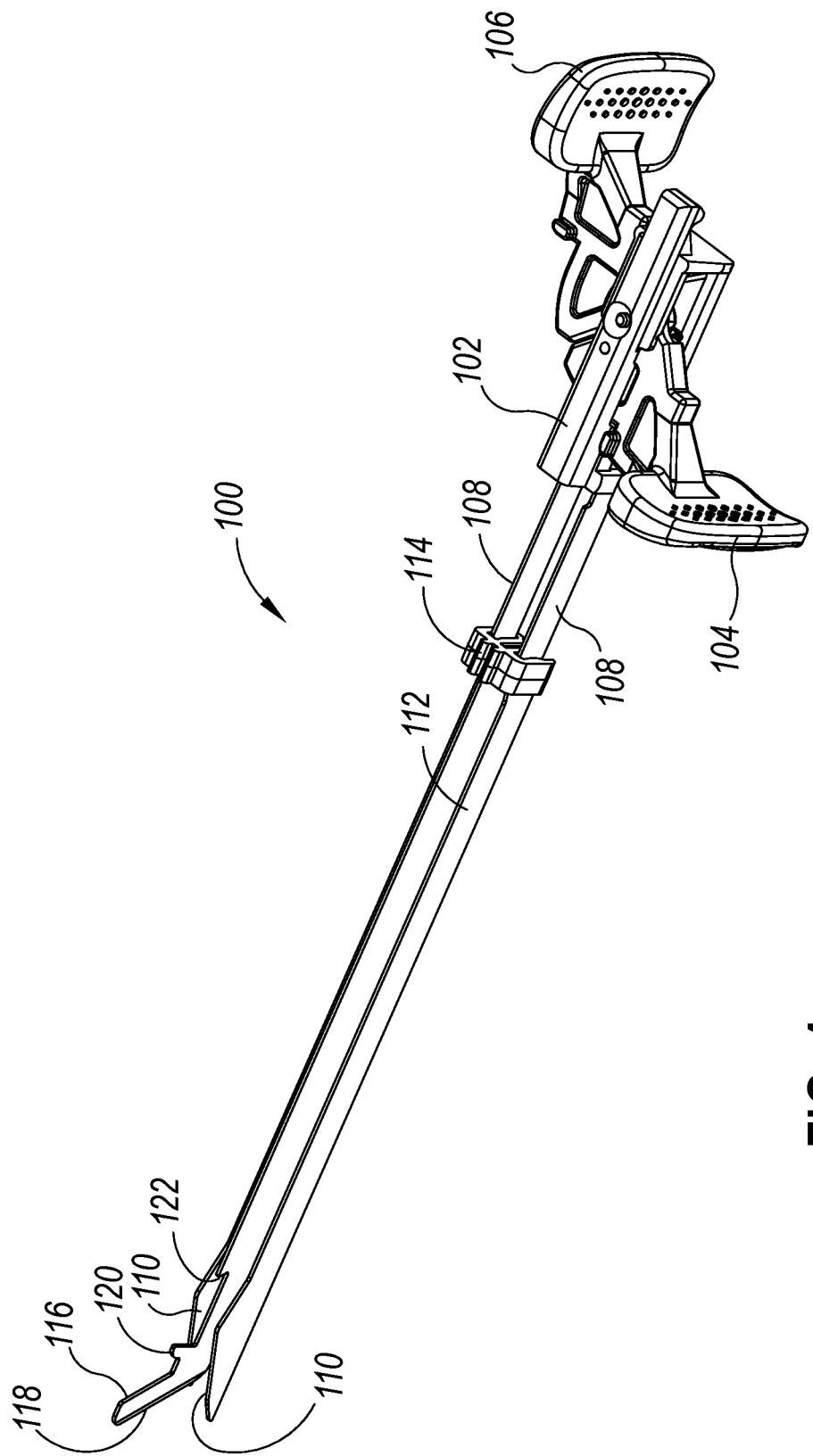

SURGICAL LINEAR CUTTER WISHBONE SEPARATION MECHANISM WITH DETENT

BACKGROUND

In some surgical operations, such as a gastrointestinal anastomosis, it may be desirable to clamp down on one or more layers of tissue, cut through the clamped layers, and simultaneously drive staples through the layers to substantially seal the severed layers of tissue together near their severed ends. One such instrument that may be used in such operations is a linear surgical stapler, also referred to as a "linear cutter." A linear surgical stapler generally includes a first half (referred to as a "cartridge half" or "reload half") having a distal jaw configured to support a staple cartridge (or "reload"), and a second half (referred to as an "anvil half") having a distal jaw that supports an anvil surface having staple forming features. The stapler further includes a moveable clamp lever configured to releasably clamp the stapler halves together. The stapler halves are configured to pivot relative to one another to receive and clamp tissue between the two distal jaws when the clamp lever is closed. A firing assembly of the stapler is configured to be actuated to cut the clamped layers and simultaneously drive staples through the tissue on either side of the cut line. After firing the stapler, the clamp lever may be opened, and the stapler halves separated to release the severed and stapled tissue.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 4 depicts a top perspective view of a firing assembly of the linear surgical stapler of FIG. 1;

Figure 1:
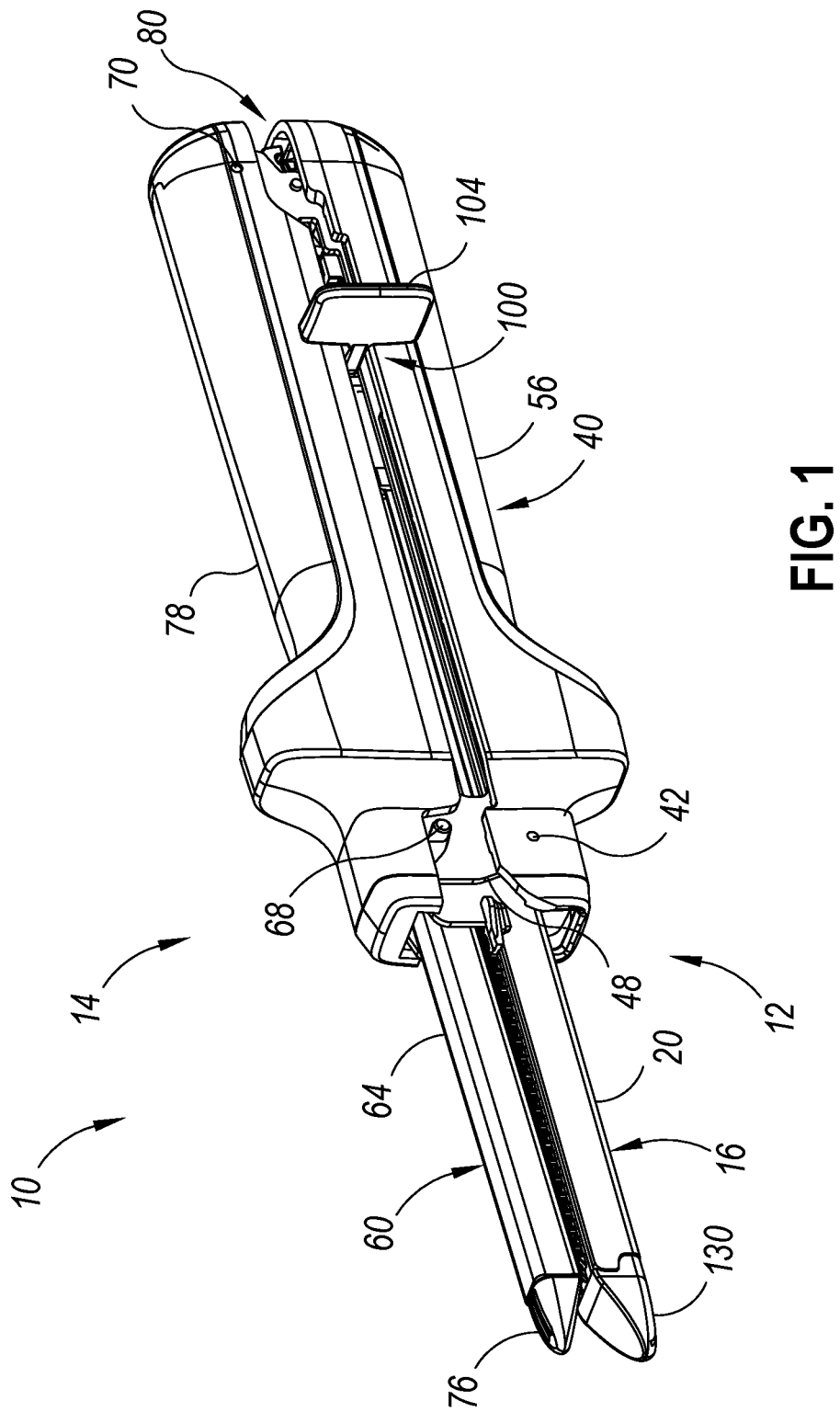
FIG. 1 depicts a perspective view of an exemplary linear surgical stapler, showing a cartridge half and an anvil half of the stapler coupled together with a clamp lever of the cartridge half in a fully closed position.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

As used herein, the terms "about" and "approximately" for any numerical values or ranges indicate a suitable dimensional tolerance that allows the part or collection of components to function for its intended purpose as described herein.

I. Exemplary Linear Surgical Stapler

A. Overview of Linear Surgical Stapler

Figure 2:
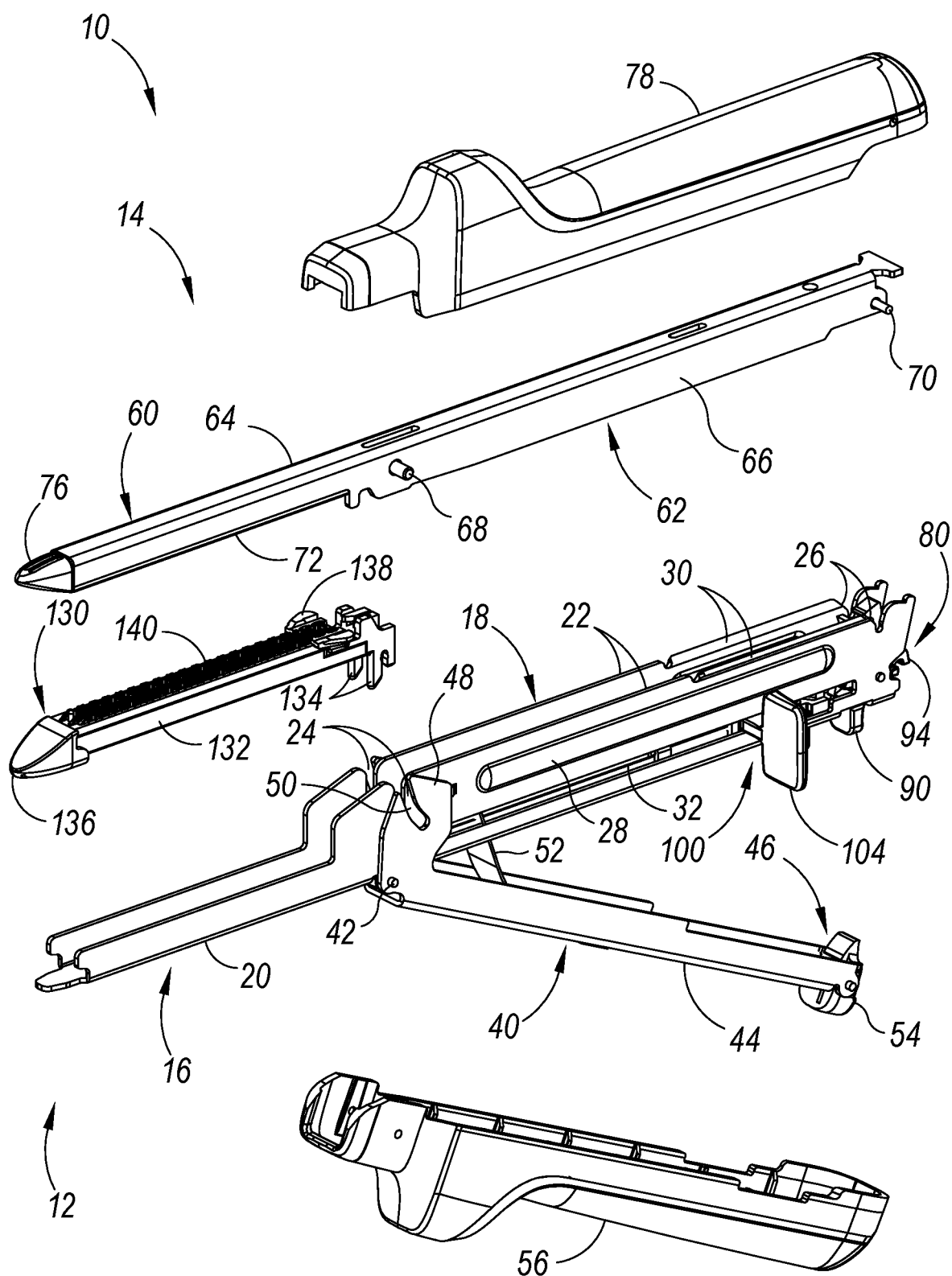
FIG. 2 depicts an exploded perspective view of the linear surgical stapler of FIG. 1.

FIGS. 1-2 show an exemplary linear surgical stapler (10) (also referred to as a "linear cutter") suitable for use in a variety of cutting and stapling procedures, such as a gastrointestinal anastomosis procedure. Linear surgical stapler (10) includes a cartridge half (12) (also referred to as a "reload half") and an anvil half (14) configured to releasably couple together to clamp tissue therebetween for simultaneous cutting and stapling of the clamped tissue.

Cartridge half (12) includes an elongate cartridge channel (16) having a proximal frame portion (18) and a distal jaw portion (20). Proximal frame portion (18) slidably retains a firing assembly (100) and includes a laterally opposed pair of upright side flanges (22). Each side flange (22) includes a vertical slot (24) arranged at a distal end thereof, and a tapered notch (26) arranged at a proximal end thereof. An outwardly projecting stiffening rib (28) extends longitudinally between the distal slot (24) and proximal notch (26) of each side flange (22) and is configured to provide the side flange (22) with enhanced stiffness. An outwardly flared upper segment (30) defines an upper edge of a proximal portion of each side flange (22) and is configured to facilitate receipt of anvil half (14) by cartridge half (12). Each side flange (22) further includes an elongate firing slot (32) extending longitudinally between proximal notch (26) and distal slot (24) along a lower side of side flange (22). Elongate firing slots (32) are configured to guide firing assembly (100) between proximal and distal positions. Firing assembly (100) is described in greater detail below in connection with FIG. 4. Distal jaw portion (20) of cartridge channel (16) is configured to receive a staple cartridge (130) (or "reload"), which may be configured in accordance with the teachings of U.S. patent application Ser. No. 16/537,005, entitled "Linear Surgical Stapler," filed on Aug. 9, 2019, the disclosure of which is incorporated by reference herein.

Cartridge half (12) further includes a clamp lever (40) (also referred to as a "latch lever") pivotably coupled to cartridge channel (16) with a clamp lever pivot pin (42), which is arranged in approximate alignment with distal slots (24) of cartridge channel side flanges (22). Clamp lever (40) includes an elongate lever arm (44) having a free proximal end (46) and a distal end that is pivotably coupled to a lower portion of cartridge channel (16) with pivot pin (42). A pair of opposed jaws (48) extend distally from the distal end of lever arm (44) alongside cartridge channel side flanges (22). Each jaw (48) includes a curved slot (50) having a closed proximal end and an open distal end configured to receive a latch pin (68) of anvil half (14), as described below.

Figure 3:
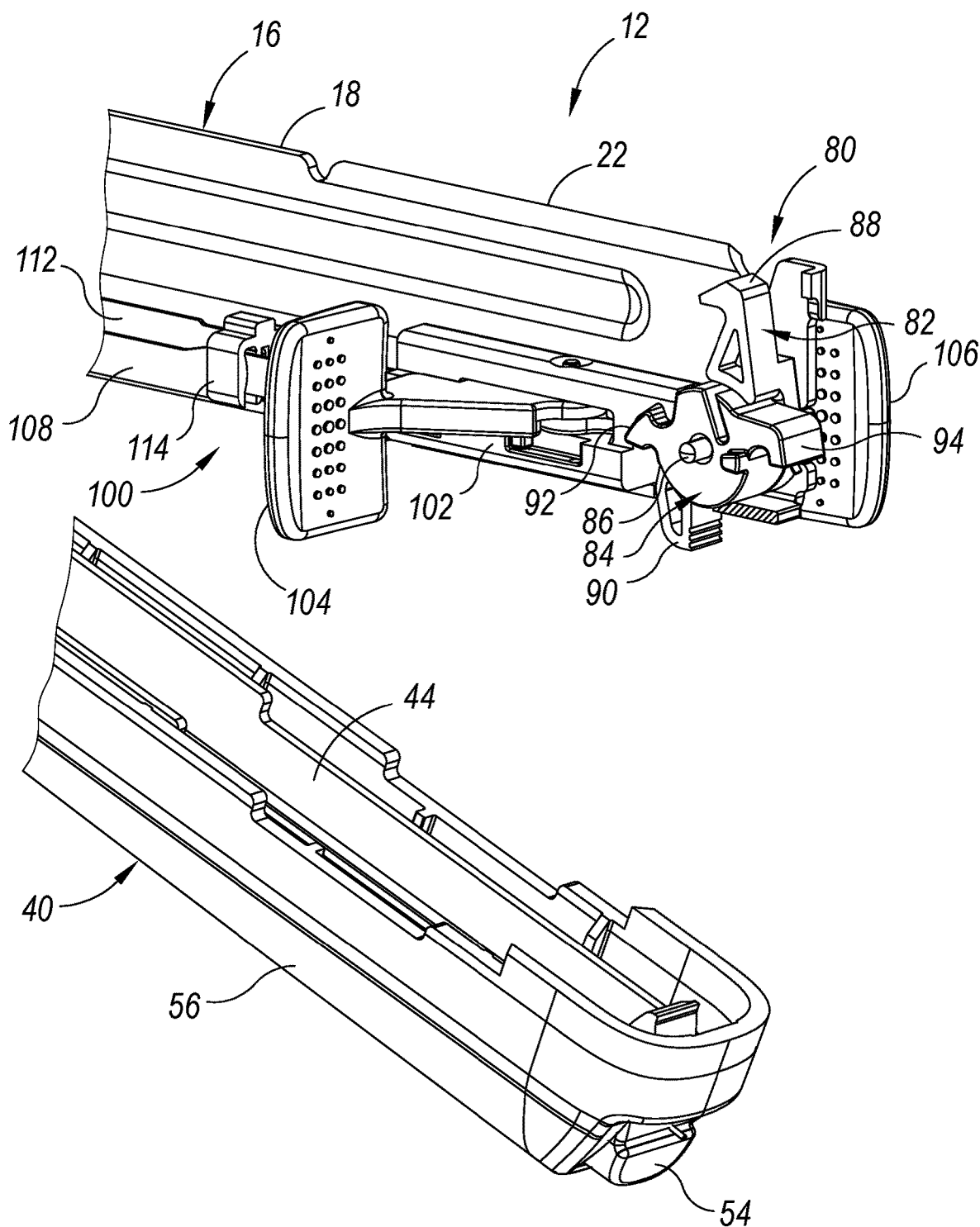
FIG. 3 depicts a perspective view of a proximal portion of the cartridge half of the linear surgical stapler of FIG. 1, showing a cartridge channel in cross-section and the clamp lever in an open position to reveal internal features of the cartridge half.

Clamp lever (40) is operable to pivot relative to cartridge channel (16) between an open position in which proximal end (46) of lever arm (44) is spaced from cartridge channel frame portion (18), and a closed position in which proximal end (46) confronts cartridge channel frame portion (18). Actuation of clamp lever (40) from the open position to the closed position operates to capture the opposed lateral ends of latch pin (68) within clamp lever jaw slots (50), and thereby clamp anvil half (14) against cartridge half (12), as shown and described below in connection with FIGS. 5C-5D. In that regard, the curvature of each jaw slot (50) defines respective upper and lower camming surfaces configured to engage and draw the respective lateral end of latch pin (68) toward cartridge channel (16) as clamp lever (40) is pivotably closed. A resilient member shown in the form of a flat spring (52) biases lever arm (44) toward the open position. Accordingly, flat spring (52) promotes disengagement of clamp lever jaws (48) from anvil half latch pin (68) upon initial advancement of clamp lever (40) from the closed position toward the open position. As best shown in FIGS. 2 and 3, clamp lever (40) further includes a latch member (54) arranged at proximal end (46) of lever arm (44). Clamp lever latch member (54) is configured to resiliently and releasably engage a proximal end of cartridge channel frame portion (18) and thereby releasably retain clamp lever (40) in the closed position, for instance while stapler (10) is being fired.

Anvil half (14) of linear surgical stapler (10) includes an elongate anvil channel (60) having a proximal frame portion (62) and a distal jaw portion (64). Proximal frame portion (62) includes a laterally opposed pair of upright side flanges (66) that are configured to be received between cartridge channel side flanges (22) when anvil half (14) is coupled with cartridge half (12). A distal latch projection in the form of latch pin (68) extends laterally through the distal ends of anvil channel side flanges (66), and a proximal pivot projection in the form of a proximal pin (70) extends laterally through the proximal ends of anvil channel side flanges (66). Anvil pins (68, 70) are configured to facilitate coupling of anvil half (14) with cartridge half (12), as described below.

Distal jaw portion (64) of anvil half (14) supports an anvil plate (72) that defines an anvil surface having a plurality of staple forming pockets (not shown) configured to deform legs of staples ejected by staple cartridge (130) when stapler (10) is fired, for example as described in greater detail in U.S. patent application Ser. No. 16/537,005, incorporated by reference above. In some versions, the anvil surface may be formed integrally with distal jaw portion (64). Distal jaw portion (64) of anvil half (14) additionally supports a tapered distal tip member (76). In some versions, distal tip member (76) may be selectively extendable relative to distal jaw portion (64) in accordance with the teachings of U.S. patent application Ser. No. 16/165,587, entitled "Decoupling Mechanism for Linear Surgical Stapler," filed on Oct. 19, 2018, the disclosure of which is incorporated by reference herein.

As shown in FIG. 2, linear surgical stapler (10) further includes a plurality of shrouds (56, 78) that cover select portions of stapler (10) and promote effective grip and manipulation of stapler (10) by an operator during use. In the present example, a clamp lever shroud (56) is affixed to and covers an outwardly facing side of clamp lever (40) such that clamp lever shroud (56) is configured to pivot with clamp lever (40) relative to cartridge channel (16). Additionally, an anvil shroud (78) is affixed to and covers an outwardly facing side of anvil channel (60). In some versions, anvil shroud (78) may be coupled with anvil channel (60) in accordance with the teachings of U.S. patent application Ser. No. 16/102,170, entitled "Clamping Assembly for Linear Surgical Stapler," filed on Aug. 13, 2018, the disclosure of which is incorporated by reference herein. It will be appreciated that in other versions, shrouds (56, 78) may be coupled with clamp lever (40) and anvil channel (60) in a variety of other suitable manners readily apparent to those of ordinary skill in the art.

As shown best in FIG. 3, a proximal end of cartridge half (12) includes a retaining assembly (80) configured to releasably retain portions of anvil half (14) and firing assembly (100). Retaining assembly (80) of the present example includes an anvil latch member (82) and a detent member (84), both of which are rotatably coupled with a proximal end of cartridge channel (16) via a laterally extending pin (86) arranged proximally of firing slots (32). A torsion spring (not shown) is configured to resiliently bias anvil latch member (82) and detent member in opposite rotational directions about the lateral axis defined by pin (86).

Anvil latch member (82) includes an upper finger (88) configured to releasably capture proximal anvil pin (70) when pin (70) is directed into proximal tapered notches (26) of cartridge channel (16), thereby coupling the proximal ends of stapler halves (12, 14). A lower end of anvil latch member (82) defines a release button (90) configured to be depressed by the operator when clamp lever (40) is in the open position to release proximal pin (70) from latch finger (88) and thereby permit separation of the proximal ends of stapler halves (12, 14). Detent member (84) includes a distal finger (88) configured to releasably capture the proximal end of a slide block (102) of firing assembly (100) when firing assembly (100) is in a proximal home position, shown in FIG. 3. Detent member (84) further includes a proximal hook (94) configured to releasably capture an upper tip of clamp lever latch member (54) while slide block (102) is positioned distally of its proximal home position, thereby preventing actuation of clamp lever latch member (54) and opening of clamp lever (40) during firing of stapler (10). When firing assembly (100) is in its proximal home position (i.e., before or after firing of stapler (10)), proximal hook (94) of detent member (84) permits clamp lever latch member (54) to rotatably disengage proximal frame portion (18) of cartridge channel (16) in response to actuation by the operator. As a result, clamp lever (40) may then be opened. Retaining assembly (80) and related components of cartridge half (12) may be further configured and operable in accordance with at least some of the teachings of U.S. patent application Ser. No. 16/102,164, entitled "Firing System for Linear Surgical Stapler," filed on Aug. 13, 2018, the disclosure of which is incorporated by reference herein.

As shown best in FIG. 4, firing assembly (100) of cartridge half (12) includes slide block (102), a pair of actuators (104, 106) (or "firing knobs") pivotably coupled to slide block (102), and a plurality of elongate beams (108, 112) extending distally from slide block (102). A pair of side beams (108) are coupled at their proximal ends to a distal end of slide block (102) and terminate distally in a pair of cam ramps (110). Cam ramps (110) are configured to engage the undersides of staple drivers (not shown) housed within staple cartridge (130) and actuate staple drivers upwardly to thereby drive (or "fire") staples from cartridge (130) into tissue clamped between staple cartridge (130) and anvil plate (72). A center beam (112) is coupled with side beams (108) via a bridge member (114) (or "knife block") spaced distally from slide block (102). Center beam (112) terminates distally in a distally angled knife member (116) having a distal cutting edge (118) configured to cut tissue clamped between the distal portions of stapler halves (12, 14). A distal portion of center beam (112) additionally includes an upwardly projecting stop element (120) proximal to knife member (116), and a distally facing lockout projection (122) proximal to stop element (120).

Each actuator (104, 106) of firing assembly (100) is configured and rotatable relative to slide block (102) between a deployed position and a retracted position such that only one actuator (104, 106) may be deployed at a time, for example as described in greater detail in U.S. patent application Ser. No. 16/102,164, incorporated by reference above. In the deployed position, an actuator (104, 106) may be driven distally by an operator to actuate firing assembly (100) distally through stapler (10) and thereby simultaneously cut and staple tissue clamped between stapler halves (12, 14).

B. Overview of Exemplary Staple Cartridge

As best shown in FIG. 2, staple cartridge (130) includes an elongate cartridge body (132) extending linearly along a longitudinal axis between a proximal end having a pair of hooks (134) and a distal end having a tapered nose (136). Proximal hooks (134) are configured to releasably capture clamp lever pivot pin (42) and extend downwardly through corresponding openings formed in a floor of cartridge channel (16) when staple cartridge (130) is seated within distal jaw portion (20) of cartridge channel (16). A pair of wing tabs (138) disposed on the lateral sides of cartridge body (132) near the proximal end are configured to facilitate insertion and removal of staple cartridge (130) relative to distal jaw portion (20). An upper side of cartridge body (132) defines a deck (140). An elongate knife slot (not shown) extends longitudinally through deck (140) along the longitudinal axis of staple cartridge (130) and is configured to slidably receive knife member (116) of firing assembly (100) therethrough in response to distal actuation thereof, described above. A rigid tissue gap post (146) is secured at a distal end of the knife slot and protrudes upwardly away from cartridge deck (140). A rounded upper end of tissue gap post (146) is configured to contact a distal end of anvil plate (72) and thereby define a tissue gap between cartridge deck (140) and anvil plate (72) when stapler halves (12, 14) are clamped together in the manner described below. Staple cartridge (130) may be configured in accordance with the teachings of U.S. patent application Ser. No. 16/537,005, incorporated by reference above.

C. Exemplary Use of Linear Surgical Stapler

Figure 5A:
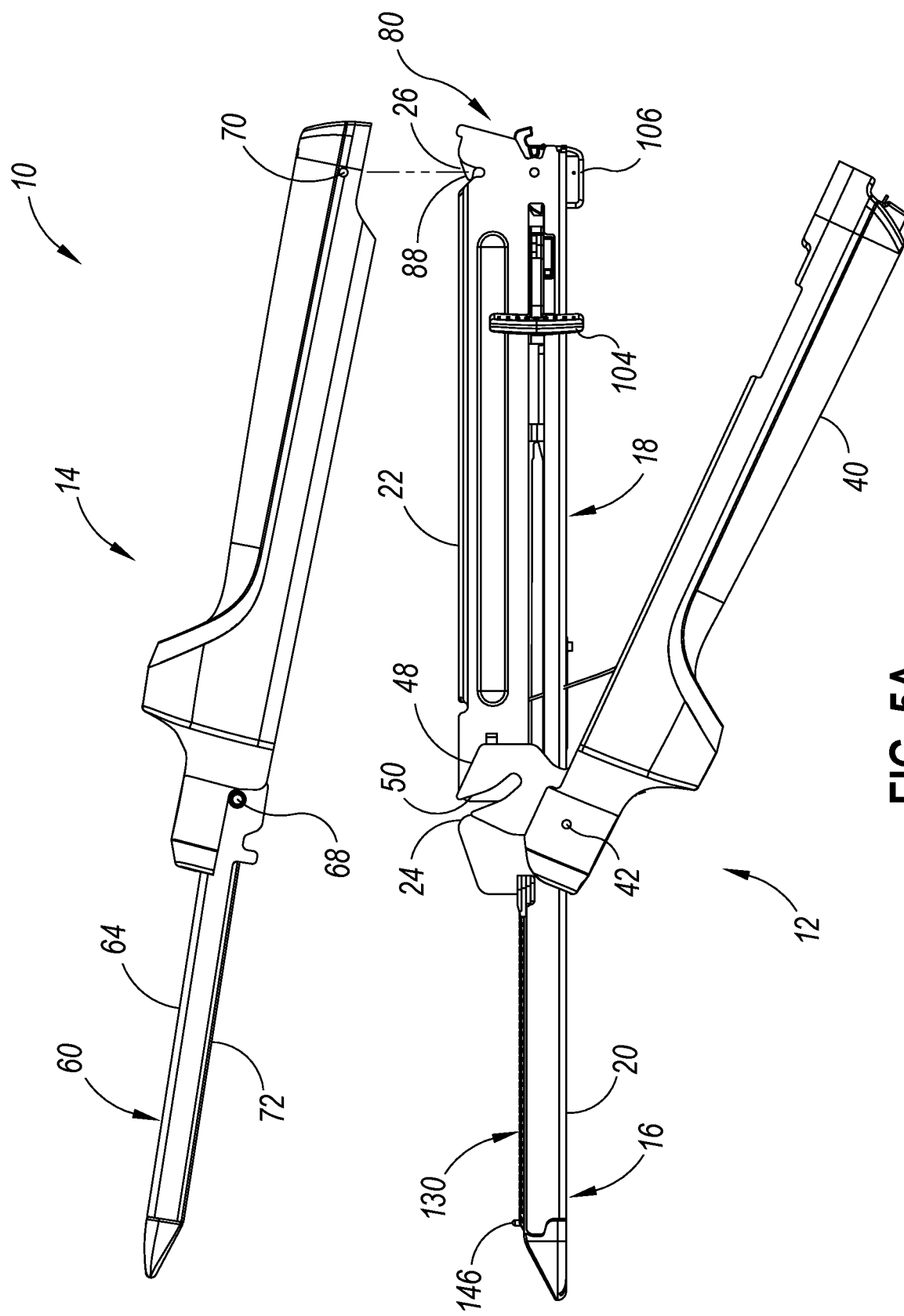
FIG. 5A depicts a side elevational view of the linear surgical stapler of FIG. 1, showing the stapler halves separated from one another.

FIGS. 5A-5E show exemplary coupling of stapler halves (12, 14) and subsequent firing of assembled stapler (10) during a surgical procedure. As shown in FIG. 5A, clamp lever (40) of cartridge half (12) is provided in the open position so that jaw slots (50) align with vertical slots (24) of cartridge channel side flanges (22). Additionally, firing assembly (100) is maintained in its proximal home position by detent member (84) of retaining assembly (80), as shown in FIG. 3 described above. At this stage, a section of tissue (not shown) to be stapled and cut may be positioned over the top of staple cartridge (130) disposed in distal jaw portion (20) of cartridge half (12). Alternatively, the tissue may be positioned over staple cartridge (130) following coupling of the proximal ends of stapler halves (12, 14), described below.

Figure 5B:
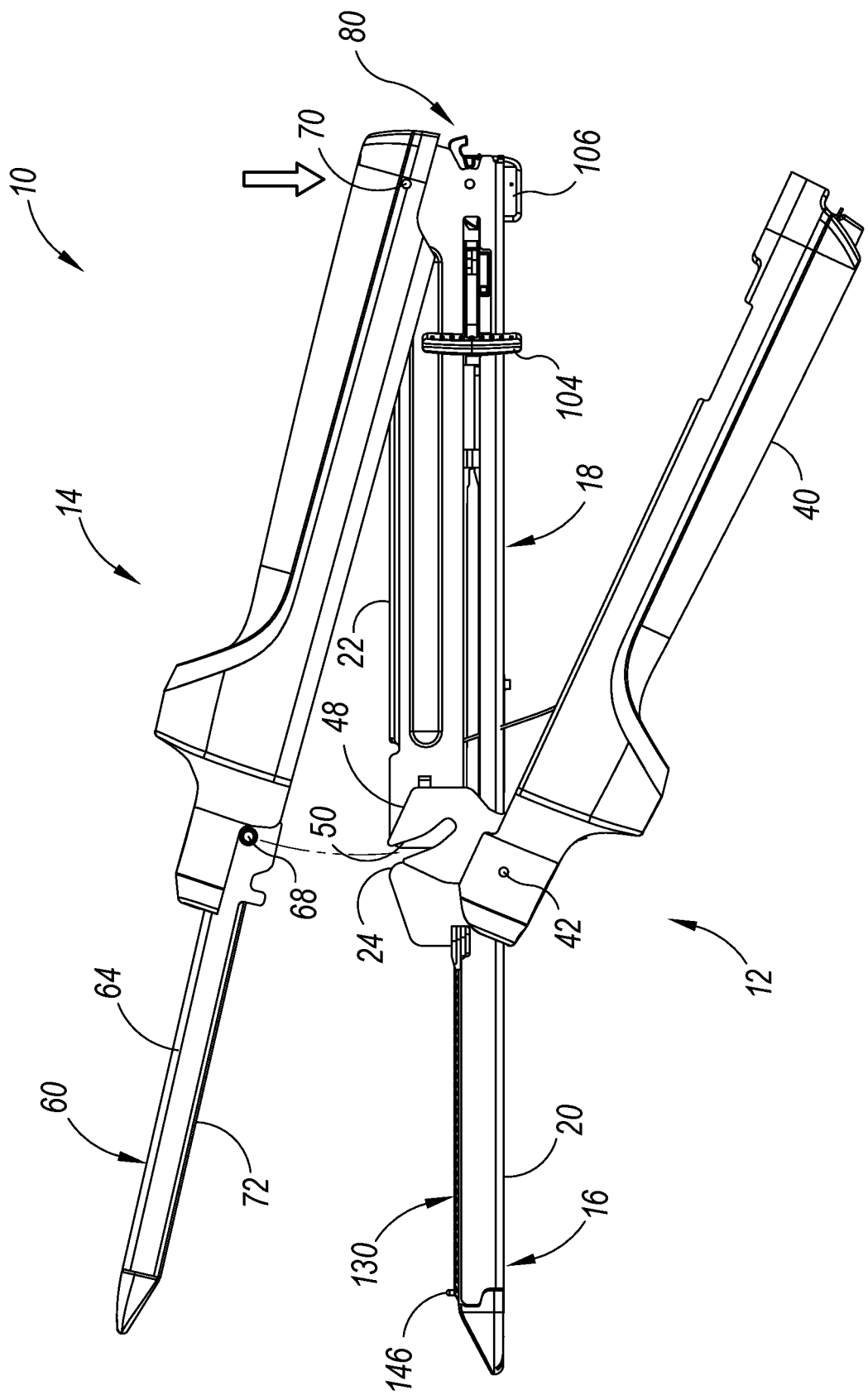
FIG. 5B depicts a side elevational view of the linear surgical stapler of FIG. 1, showing proximal ends of the stapler halves coupled together.
Figure 5C:
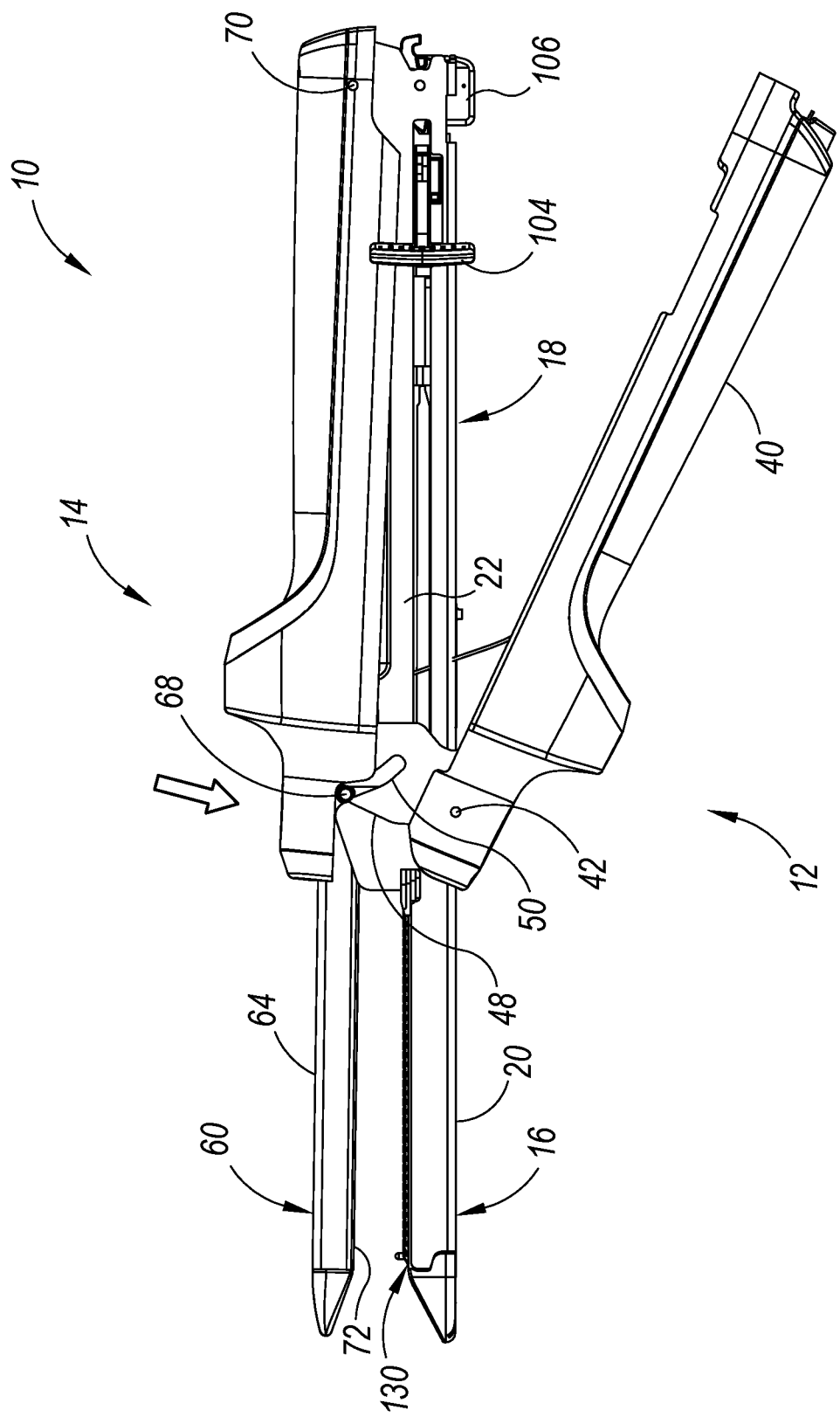
FIG. 5C depicts a side elevational view of the linear surgical stapler of FIG. 1, showing a distal pin of the anvil half being received by clamp lever jaws of the cartridge half.

As shown in FIG. 5A-5B, the proximal ends of stapler halves (12, 14) are aligned with one another and proximal anvil pin (70) is directed downwardly into proximal tapered notches (26) of cartridge channel (16) to engage upper finger (88) of anvil latch member (82). This engagement forces anvil latch member (82) to resiliently rotate clockwise, thus enabling upper finger (88) of anvil latch member (82) to capture anvil pin (70) and thereby releasably couple together the proximal ends of stapler halves (12, 14), as seen in FIG. 5B. As shown in FIG. 5C, and with clamp lever (40) remaining in the open position, anvil half (14) is rotated toward cartridge half (12) about proximal anvil pin (70) so that distal latch pin (68) of anvil half (14) is received into vertical slots (24) of cartridge channel side flanges (22) and jaw slots (50) of clamp lever (40). Distal jaw portions (20, 64) of stapler halves (12, 14) are now in a partially approximated state such that tissue received therebetween may be finally adjusted before clamping.

Figure 5D:
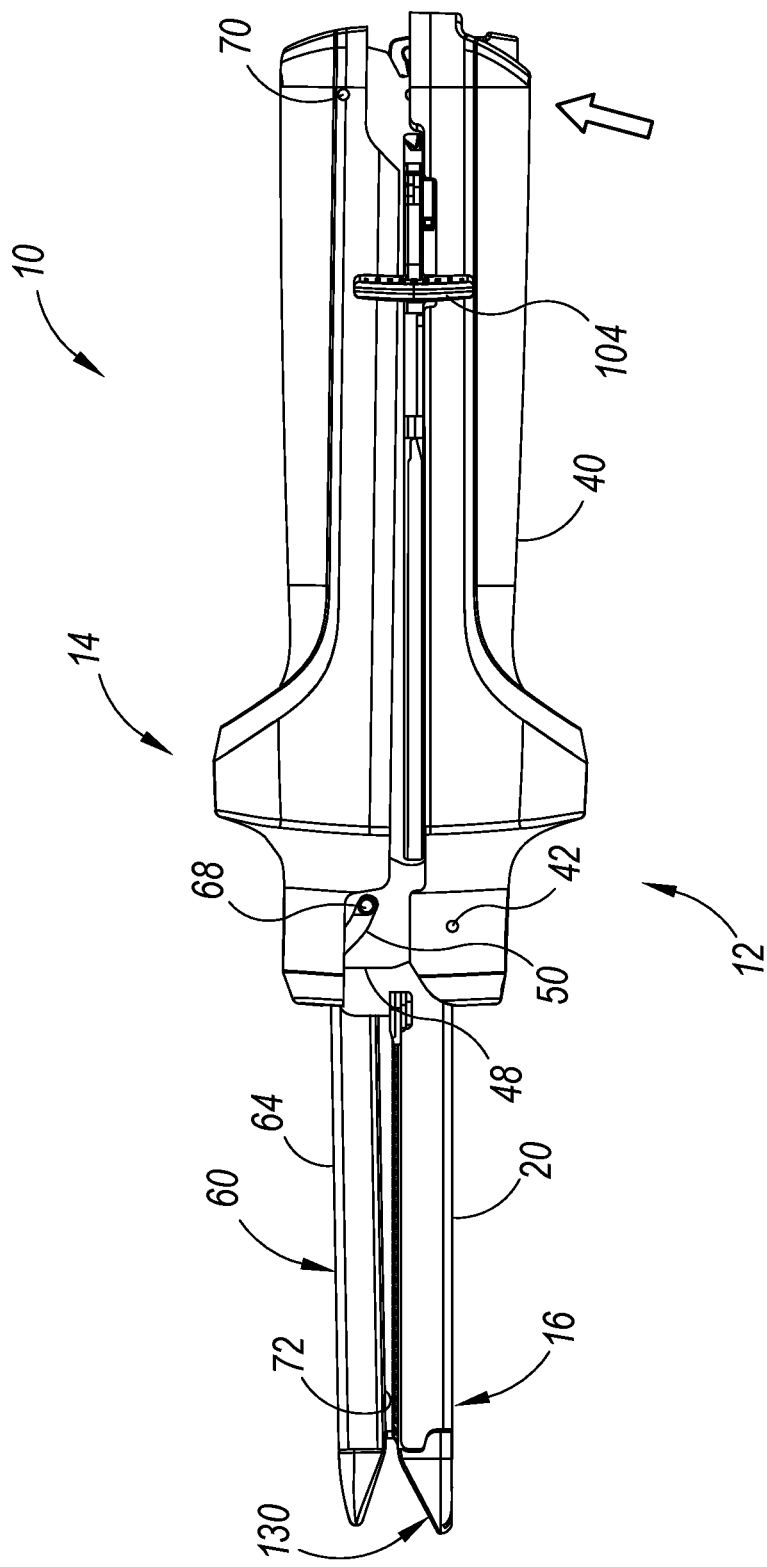
FIG. 5D depicts a side elevational view of the linear surgical stapler of FIG. 1, showing closure of the clamp lever to fully clamp the stapler halves together.

As shown in FIG. 5D, clamp lever (40) is closed to draw anvil latch pin (68) against the closed proximal ends of jaw slots (50) and thereby fully clamp anvil half (14) against cartridge half (12), with tissue (not shown) clamped between staple cartridge (130) and anvil plate (72). A slight transverse gap is defined between staple cartridge (130) and anvil plate (72) by tissue gap post (146) of staple cartridge (130), thus accommodating the tissue therebetween with a predetermined degree of tissue compression. As shown in FIGS. 5A and 5B, tissue gap post (146) is disposed at a distal end of staple cartridge (130) and is configured to contact a distal end of anvil plate (72) when stapler (10) is in the fully clamped state shown in FIG. 5D, for example as described in greater detail in U.S. patent application Ser. No. 16/537,005, incorporated by reference above.

Figure 5E:
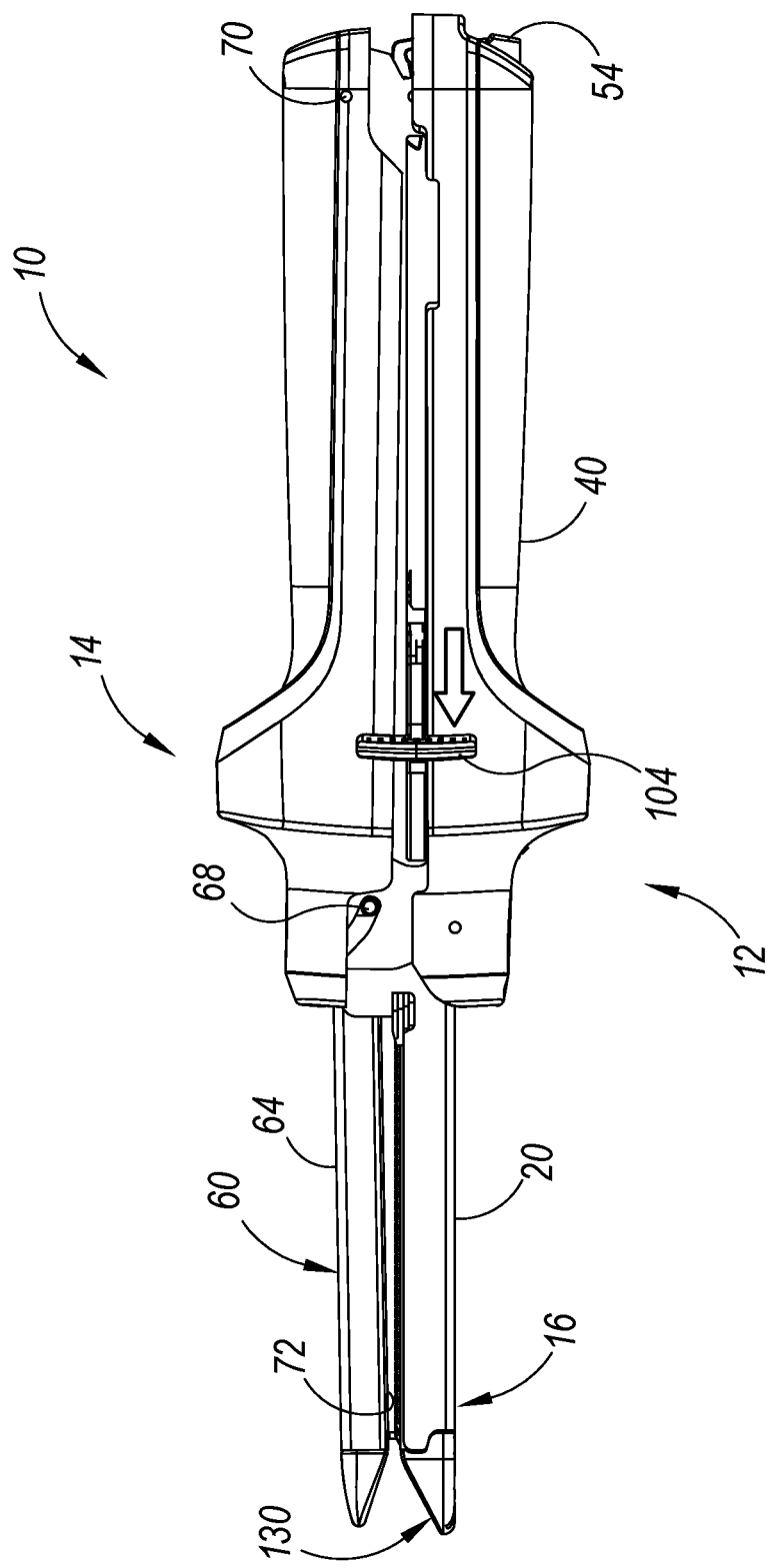
FIG. 5E depicts a side elevational view of the linear surgical stapler of FIG. 1, showing distal actuation of the firing assembly while the stapler halves are in the fully clamped state.

As shown in FIG. 5E, upon reaching the fully clamped state, stapler (10) may be fired by driving a deployed actuator (104, 106) of firing assembly (100) distally along proximal frame portion (18) of cartridge half (12). As described above in connection with FIG. 4, this action causes elongate beams (108, 112) of firing assembly (100) to translate distally through corresponding channels formed in staple cartridge (130) and thereby fire staples into the clamped tissue via cam ramps (110) and staple drivers, and simultaneously cut the clamped tissue with knife member (116). Following completion of the firing stroke, firing assembly (100) is returned to its proximal home position via the actuator (104, 106). Clamp lever latch member (54) may then be depressed to release the proximal end of clamp lever (40) from cartridge channel (16), thus permitting clamp lever (40) to be re-opened. Then, release button (90) of retaining assembly (80) may be depressed to release anvil half (14) from cartridge half (12) so that stapler halves (12, 14) may be separated from one another, thereby releasing the newly stapled and severed tissue. It will be understood that in some versions, stapler (10) may include features that promote decoupling of stapler halves (12, 14) similar to those features disclosed in U.S. patent application Ser. No. 16/165,587, incorporated by reference above.

II. Exemplary Surgical Linear Cutter Wishbone Separation Mechanisms

As described above in connection with surgical stapler (10), a pivotable coupling is established between the proximal ends of stapler halves (12, 14) when anvil pin (70) is captured by upper finger (88) of anvil latch member (82). Release button (90) of retaining assembly (80) may be subsequently depressed to release anvil half (14) from cartridge half (12) so that stapler halves (12, 14) may be separated from one another.

In some instances, it may be desirable to provide a linear surgical stapler with an open state in which respective elongate members of the stapler halves assume a predetermined maximum angular orientation relative to one another and remain releasably coupled together at their proximal ends (also referred to as a "hang open" or "open aperture" state), such that the stapler in the open state can be easily manipulated by an operator with a single hand. It may also be desirable for the operator to be able to separate the halves by intuitively pulling or prying the halves apart from each other without first depressing a retaining assembly release button. Such a configuration may protect against unintentional decoupling of the stapler halves during single-handed manipulation of the stapler while also simplifying desired separations of the stapler halves. The following description provides several illustrative examples of variations of surgical stapler (10) that may provide such functionality.

Figure 6:
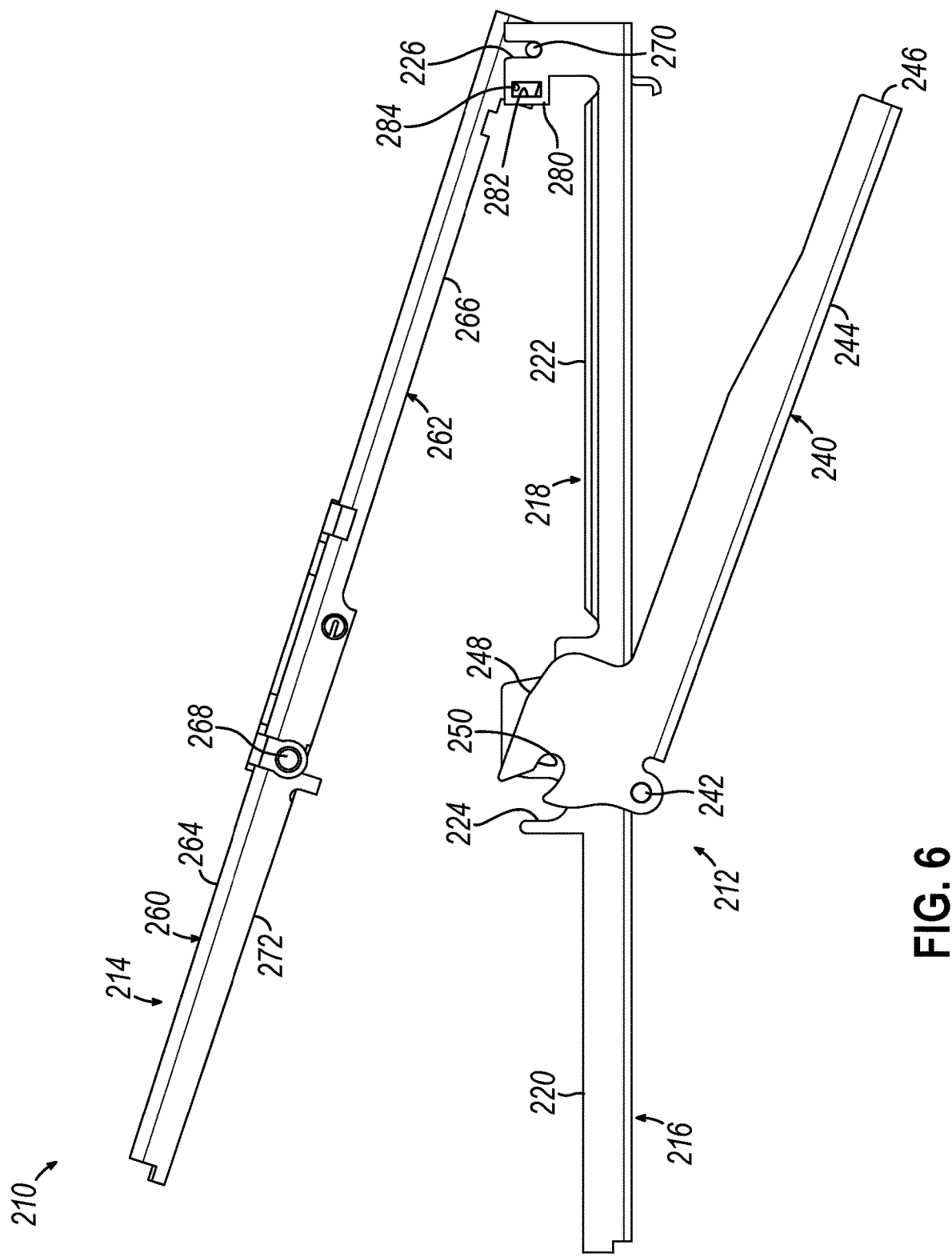
FIG. 6 depicts a side elevational view of another exemplary linear surgical stapler having an aperture positioned on the cartridge half and a corresponding detent positioned on the anvil half, showing the stapler halves rotated relative to each other in an open state in which the proximal ends of the stapler halves are coupled together and the distal ends of the stapler halves are spaced apart.

A. Exemplary Linear Cutter Separation Mechanism with Detent and Corresponding Aperture FIGS. 6-6C show an exemplary surgical stapler (210) including a cartridge half (212) and an anvil half (214) configured to remain releasably coupled together at their proximal ends in an open state in which respective elongate members of the stapler halves (212, 214) assume a predetermined maximum angular orientation relative to one another, and further configured to be pulled or pried apart from each other to allow separation of stapler halves (212, 214) from each other. Stapler (210) is similar to stapler (10) described above except as otherwise described below.

Cartridge half (212) of linear surgical stapler (210) includes an elongate cartridge channel (216) having a proximal frame portion (218) and a distal jaw portion (220). Proximal frame portion (218) slidably retains a firing assembly (not shown) and includes a laterally opposed pair of upright side flanges (222). Each side flange (222) includes a vertical slot (224) arranged at a distal end thereof, and a notch (226) arranged at a proximal end thereof. In the example shown, each side flange (222) extends upwardly to varying degrees along the length of proximal frame portion (218), such that the proximal portion of each side flange (222) defining the respective notch (226) is generally goalpost-shaped. It will be appreciated that side flanges (222) may be configured in any other suitable manner. For example, one or both side flanges (222) may extend upwardly in a more uniform manner along the length of proximal frame portion (218) as shown in connection with stapler (10).

Cartridge half (212) further includes a clamp lever (240) pivotably coupled to cartridge channel (216) with a clamp lever pivot pin (242), which is arranged in approximate alignment with distal slots (224) of cartridge channel side flanges (222). Clamp lever (240) includes an elongate lever arm (244) having a free proximal end (246) and a distal end that is pivotably coupled to a lower portion of cartridge channel (216) with pivot pin (242). A pair of opposed jaws (248) extend distally from the distal end of lever arm (244) alongside cartridge channel side flanges (222). Each jaw (248) includes a curved slot (250) having a closed proximal end and an open distal end configured to receive a latch pin (268) of anvil half (214), as described above in connection to FIGS. 5A-5E.

Anvil half (214) of linear surgical stapler (210) includes an elongate anvil channel (260) having a proximal frame portion (262) and a distal jaw portion (264). Proximal frame portion (262) includes a laterally opposed pair of upright side flanges (266) that are configured to be received between cartridge channel side flanges (222) when anvil half (214) is coupled with cartridge half (212). A distal latch projection in the form of latch pin (268) extends laterally through the distal ends of anvil channel side flanges (266), and a proximal pivot projection in the form of a round (e.g., circular) proximal pin (270) extends laterally through the proximal ends of anvil channel side flanges (266). Distal jaw portion (264) of anvil half (214) supports an anvil plate (272) that defines an anvil surface having a plurality of staple forming pockets (not shown) configured to deform legs of staples ejected by a staple cartridge (not shown) when stapler (210) is fired.

In one example, linear surgical stapler (210) may further include one or more shrouds (e.g., a clamp lever shroud and/or an anvil shroud) that cover select portions of stapler (210) and promote effective grip and manipulation of stapler (210) by an operator during use.

Figure 6A:
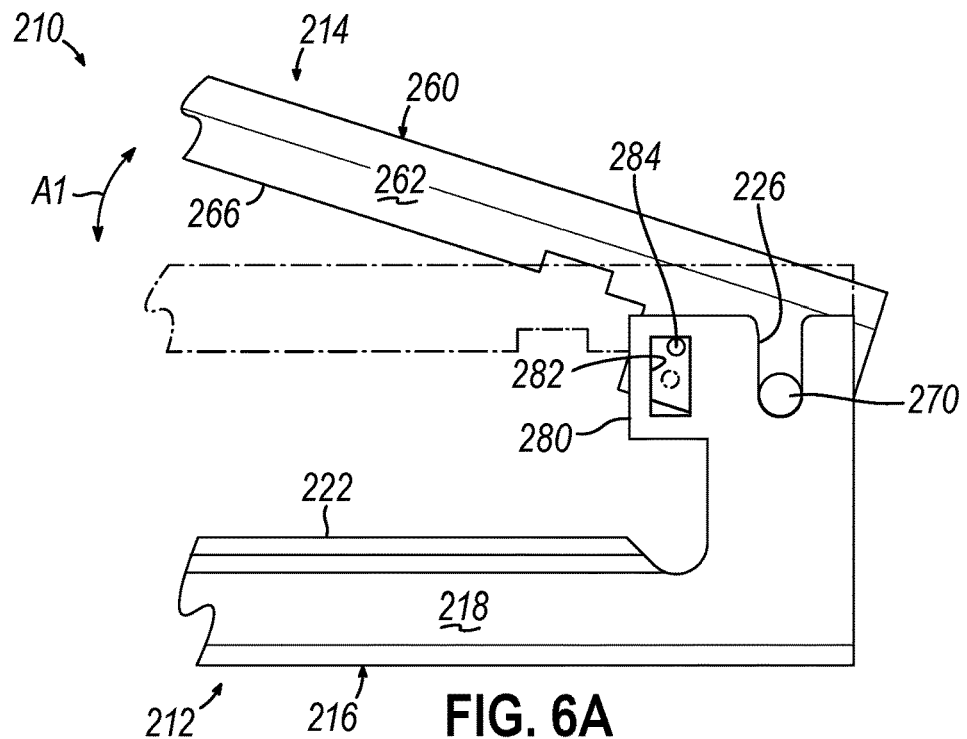
FIG. 6A depicts a side elevational view of a proximal end of the linear surgical stapler of FIG. 6, showing the detent of the anvil half inserted within the aperture of the cartridge half for coupling the stapler halves at their proximal ends during rotation of the stapler halves between the open and clamped states.
Figure 6B:
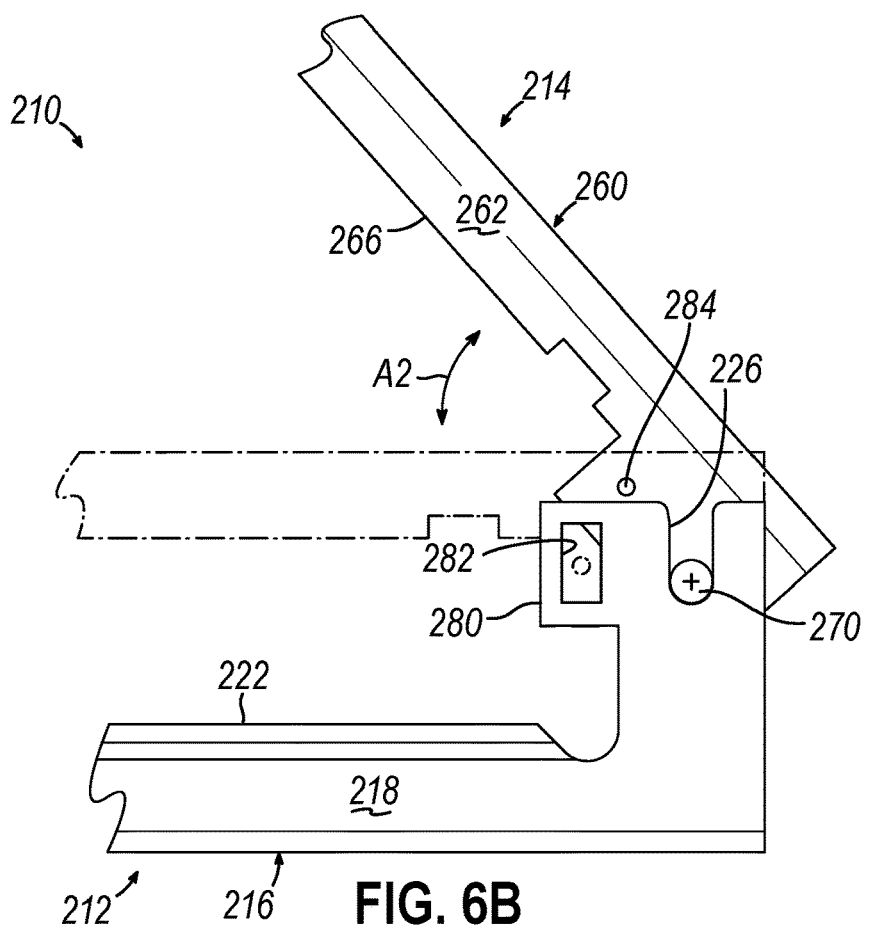
FIG. 6B depicts a side elevational view of the proximal end of the linear surgical stapler of FIG. 6, showing insertion of the detent of the anvil half into the aperture of the cartridge half during rotational approximation of the stapler halves.
Figure 6C:
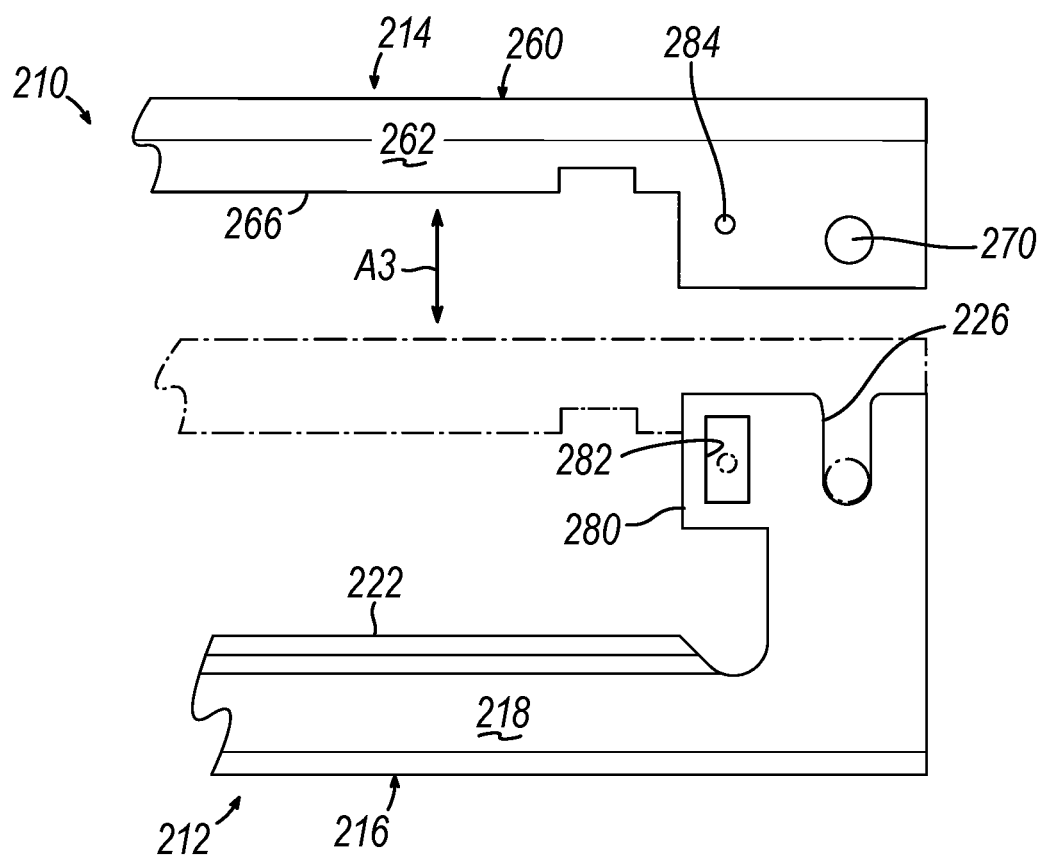
FIG. 6C depicts a side elevational view of the proximal end of the linear surgical stapler of FIG. 6, showing insertion of the detent of the anvil half into the aperture of the cartridge half during linear approximation of the stapler halves.

As shown best in FIGS. 6A-6C, a proximal end of cartridge half (212) includes at least one window frame (280) defining an aperture (282) configured to releasably retain a portion of anvil half (214). Window frame (280) of the present example is positioned on a side flange (222) of proximal frame portion (218) of cartridge channel (216) and, more particularly, extends distally from the goalpost-shaped proximal portion of side flange (222) defining the respective notch (226). In one example, window frame (280) may be integrally formed together with side flange (222) as a unitary piece. For example, window frame (280) and side flange (222) may be stamped together on cartridge channel (216). In the example shown, aperture (282) has a generally rectangular shape with longitudinally-extending upper and lower peripheral edges and vertically-extending proximal and distal peripheral edges. However, it will be appreciated that aperture (282) may be provided with any other suitable shape and may be only partially surrounded by peripheral edges (e.g., open-ended). For example, the lower and/or distal peripheral edges may be omitted, and/or the upper peripheral edge may be arched in the longitudinal direction.

As shown, a proximal end of anvil half (214) includes at least one detent member (284) configured to selectively engage window frame (280) for facilitating releasable coupling of stapler halves (212, 214). Detent member (284) of the present example is positioned on and extends laterally outwardly from a side flange (266) of proximal frame portion (262) of anvil channel (260) such that detent member (284) is capable of extending laterally into aperture (282). In one example, detent member (284) may be integrally formed together with side flange (266) as a unitary piece. For example, detent member (284) and side flange (266) may be stamped together on anvil channel (260).

As best shown in FIG. 6A, aperture (282) of window frame (280) is configured to releasably and movably capture detent member (284) when proximal anvil pin (270) is received within proximal notches (226) with anvil half (214)

oriented relative to cartridge half (212) about proximal anvil pin (270) within a predetermined angular range, thereby coupling the proximal ends of stapler halves (212, 214). More particularly, aperture (282) is sized and configured to permit movement of detent member (284) therewithin to accommodate rotation of anvil half (214) about proximal anvil pin (270) through the predetermined angular range.

In this regard, one or more peripheral edges of aperture (282) may be configured to selectively abut detent member (284) to at least partially define one or more limits of the predetermined angular range. For example, an upper peripheral edge or shoulder of aperture (282) may be configured to selectively frictionally engage or abut detent member (284) in response to rotation of anvil half (214) away from cartridge half (212) to a predetermined maximum orientation to assist in preventing inadvertent decoupling of stapler halves (212, 214), such as during single-handed manipulation of stapler (210). In this manner, such interaction between detent member (284) and the upper peripheral edge of aperture (282) may define an open state of stapler (210) by allowing cartridge half (212) and anvil half (214) to remain releasably coupled together at their proximal ends while their distal ends are spaced apart by an open gap. The remaining peripheral edges of aperture (282) may be configured to guide or otherwise permit movement of detent member (284) during rotation of anvil half (214) away from the upper peripheral edge of aperture (282) toward cartridge half (212) about proximal anvil pin (270) and thereby allow stapler (210) to reach the clamped state described above in connection to FIGS. 5A-5E. Thus, interaction between detent member (284) and aperture (282) may assist in reliably coupling anvil half (214) to cartridge half (212) during rotation of anvil half (214) about proximal anvil pin (270) between the open and clamped states, as indicated by first arrow (A1) in FIG. 6A.

As best shown in FIGS. 6B and 6C, window frame (280) and detent member (284) are sized relative to each other (e.g., in the lateral direction) to permit selective overriding of the interaction between detent member (284) and the upper peripheral edge of aperture (282) upon application of a threshold separating (e.g., pulling or prying) force applied between stapler halves (212, 214) to thereby withdraw detent member (284) from aperture (282) and separate stapler halves (212, 214) from each other. Likewise, window frame (280) and detent member (284) are sized relative to each other to permit selective overriding of any interaction between detent member (284) and an upper surface of window frame (280) upon application of a threshold approximating force applied between stapler halves (212, 214) to thereby insert detent member (284) into aperture (282) and couple stapler halves (212, 214) to each other. Such threshold forces may be applied rotationally about proximal anvil pin (270) (e.g., with a "scissors" motion), as indicated by second arrow (A2) in FIG. 6B, or may be applied linearly with stapler halves (212, 214) parallel to each other, as indicated by third arrow (A3) in FIG. 6C.

While a single window frame (280) and a single corresponding detent member (284) are shown positioned on single cartridge and anvil side flanges (222, 266), respectively, cartridge half (212) may include a laterally opposed pair of window frames (280) positioned on respective cartridge side flanges (222) and anvil half (214) may likewise include a laterally opposed pair of detent members (284) positioned on respective anvil side flanges (266). Also, while the illustrated window frame (280) is positioned on cartridge half (212) and the illustrated detent member (284) is positioned on anvil half (214), it will be appreciated that an inverse arrangement may be used such that window frame (280) is positioned on anvil half (214) and detent member (284) is positioned on cartridge half (212) (e.g., extending laterally inwardly from a respective side flange (222)).

During operation, the operator may initially couple stapler halves (212, 214) together at their proximal ends by positioning proximal anvil pin (270) within notches (226) and by applying a threshold approximating force between stapler halves (212, 214) sufficient to override any interaction between detent member (284) and the upper surface of window frame (280) to thereby insert detent member (284) into aperture (282), such as in either manner shown in FIG. 6B or 6C. The operator may subsequently rotate anvil half (214) relative to cartridge half (212) about proximal anvil pin (270) as desired within the predetermined angular range, such as between the open and clamped states as shown in FIG. 6A, while stapler halves (212, 214) remain reliably coupled to each other to perform a cutting and/or stapling procedure. If desired, the operator may selectively separate stapler halves (212, 214) from each other by applying a threshold separating force between stapler halves (212, 214) sufficient to override the interaction between detent member (284) and the upper peripheral edge of aperture (282) to thereby withdrawn detent member (284) from aperture (282), such as in either manner shown in FIG. 6B or 6C.

Figure 7A:
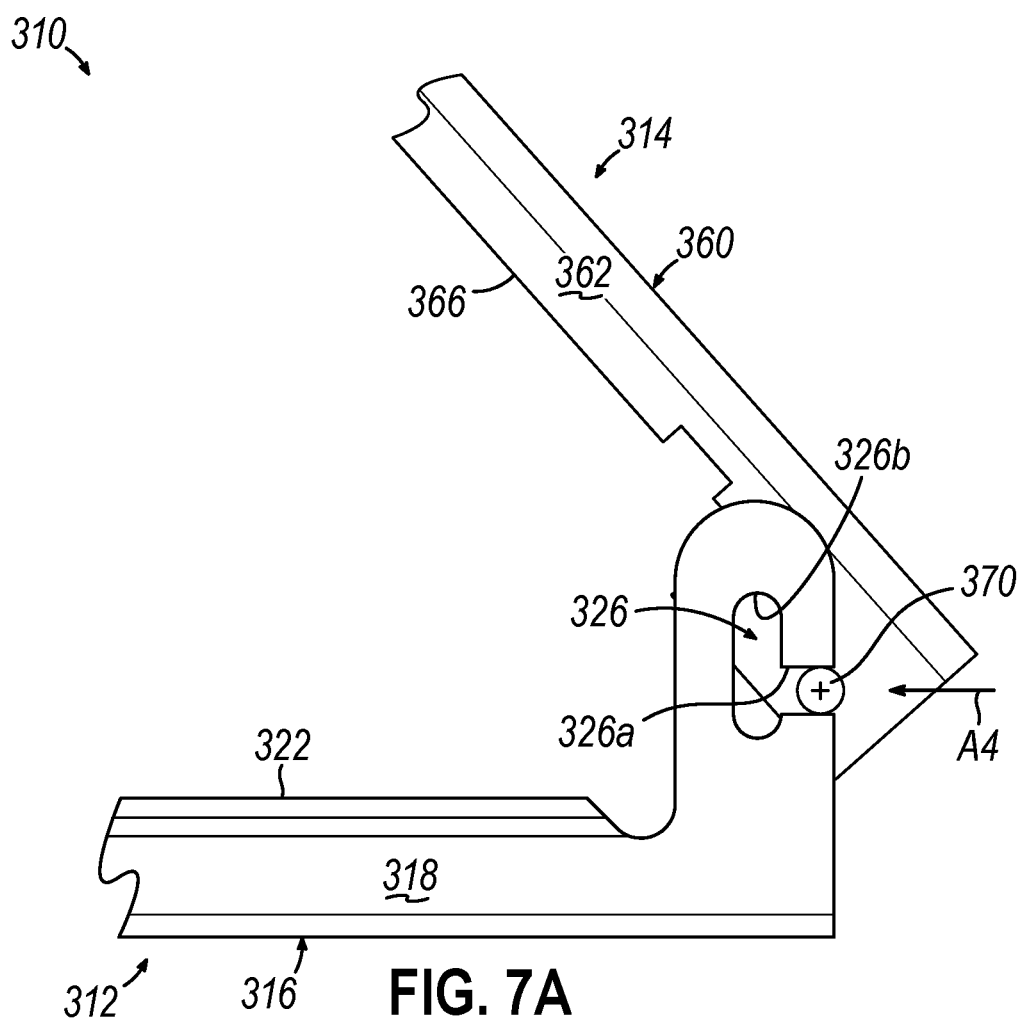
FIG. 7A depicts a side elevational view of a proximal end of another exemplary linear surgical stapler having a cartridge half with a proximally-facing multi-stage notch, showing distally-directed insertion of a proximal anvil pin into the notch.
Figure 7B:
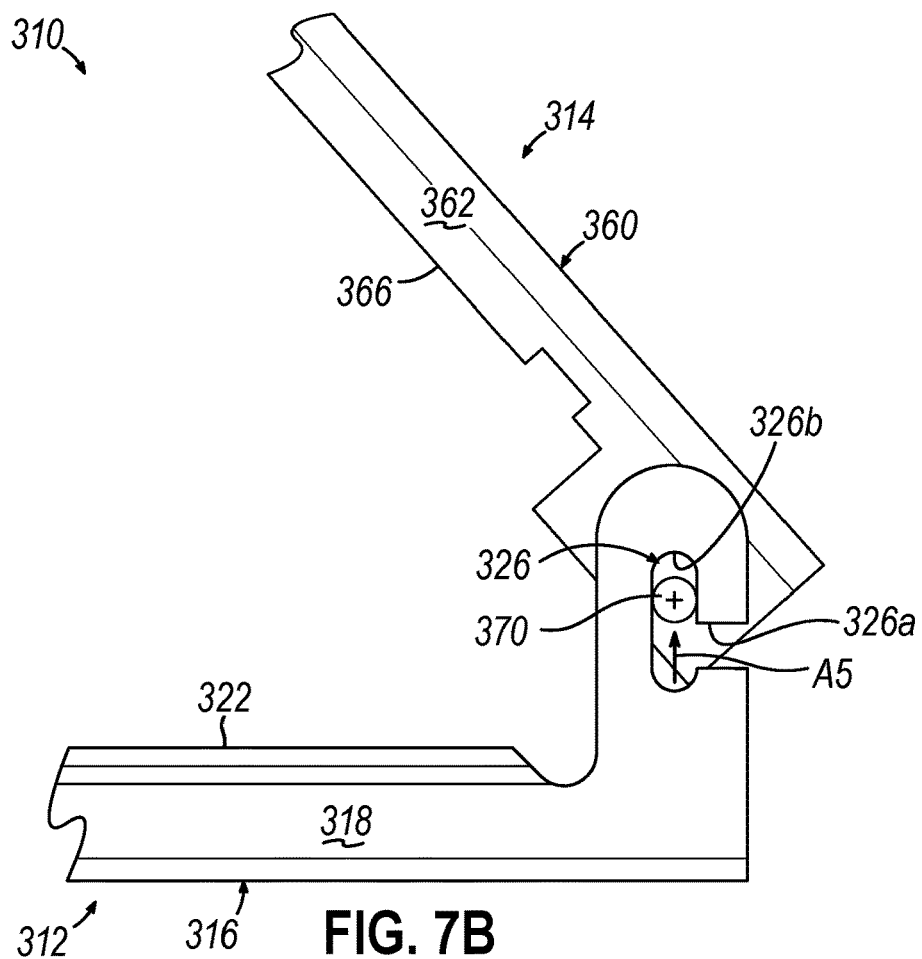
FIG. 7B depicts a side elevational view of the proximal end of the linear surgical stapler of FIG. 7A, showing upward translation of the proximal anvil pin within the notch.
Figure 7C:
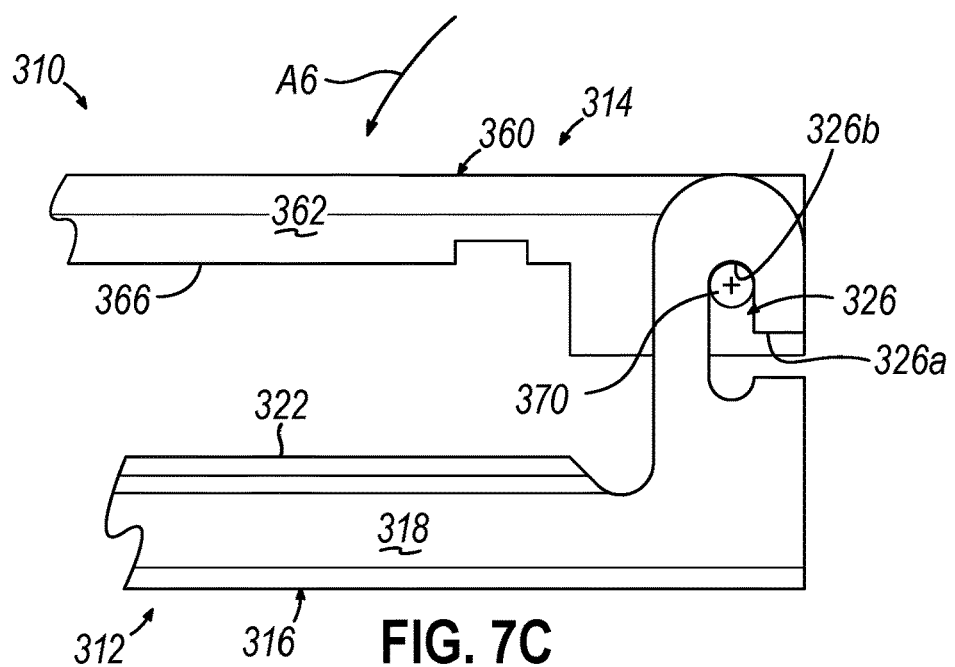
FIG. 7C depicts a side elevational view of the proximal end of the linear surgical stapler of FIG. 7A, showing rotation of the anvil half toward the cartridge half for clamping the stapler halves together.

B. Exemplary Linear Cutter Separation Mechanism with Proximally-Facing Anvil Pin Receiving Notch on Cartridge Half In some instances, it may be desirable to provide a surgical stapler separation mechanism which enables coupling and separation of the stapler halves to be performed from a rear (e.g., proximal) side of the stapler. FIGS. 7A-7C show another exemplary surgical stapler (310) including a cartridge half (312) and an anvil half (314) that are configured in such a manner, and which are similar in structure and function to stapler (210) described above except as otherwise described below.

Cartridge half (312) includes an elongate cartridge channel (316) having a proximal frame portion (318) including a laterally opposed pair of upright side flanges (322), each including a notch (326) arranged at a proximal end thereof. Anvil half (314) includes an elongate anvil channel (360) having a proximal frame portion (362) including a laterally opposed pair of upright side flanges (366) that are configured to be received between cartridge channel side flanges (322) when anvil half (314) is coupled with cartridge half (312). A proximal pivot projection in the form of a round (e.g., circular) proximal pin (370) extends laterally through the proximal ends of anvil channel side flanges (366).

In the example shown, each notch (326) is multi-stage and generally faces proximally. More particularly, each notch (326) includes a first notch portion (326a) extending distally from an open end positioned on a proximal surface of the respective side flange (322) to a second notch portion (326b) extending vertically between upper and lower closed ends, such that each notch (326) is generally L-shaped for facilitating releasable coupling of stapler halves (312, 314).

In this regard, each first notch portion (326a) is configured to receive proximal anvil pin (370) as anvil half (314) is translated distally from a position proximal to cartridge half (312) with anvil half (314) oriented away from cartridge half (312), as indicated by fourth arrow (A4) in FIG. 7A, to thereby position proximal anvil pin (370) at or near the lower closed end of the respective second notch portion (326b). Each second notch portion (326b) is configured to receive proximal anvil pin (370) as anvil half (314) is subsequently translated upwardly with anvil half (314) oriented away from cartridge half (312), as indicated by fifth arrow (A5) in FIG. 7B, to thereby position proximal anvil pin (370) at or near the upper closed end of the second notch portion (326b). The upper closed end of each second notch portion (326b) may be configured to position proximal anvil pin (370) at a predetermined location, whereat rotation of anvil half (314) toward cartridge half (312) about proximal anvil pin (370) permits the distal latch pin of anvil half (314) to be received into the vertical slots of cartridge channel side flanges (322) and/or jaw slots of the clamp lever (not shown) for locking the distal latch pin, as indicated by sixth arrow (A6) in FIG. 7C, to thereby reliably couple anvil half (314) to cartridge half (312).

Figure 8A:
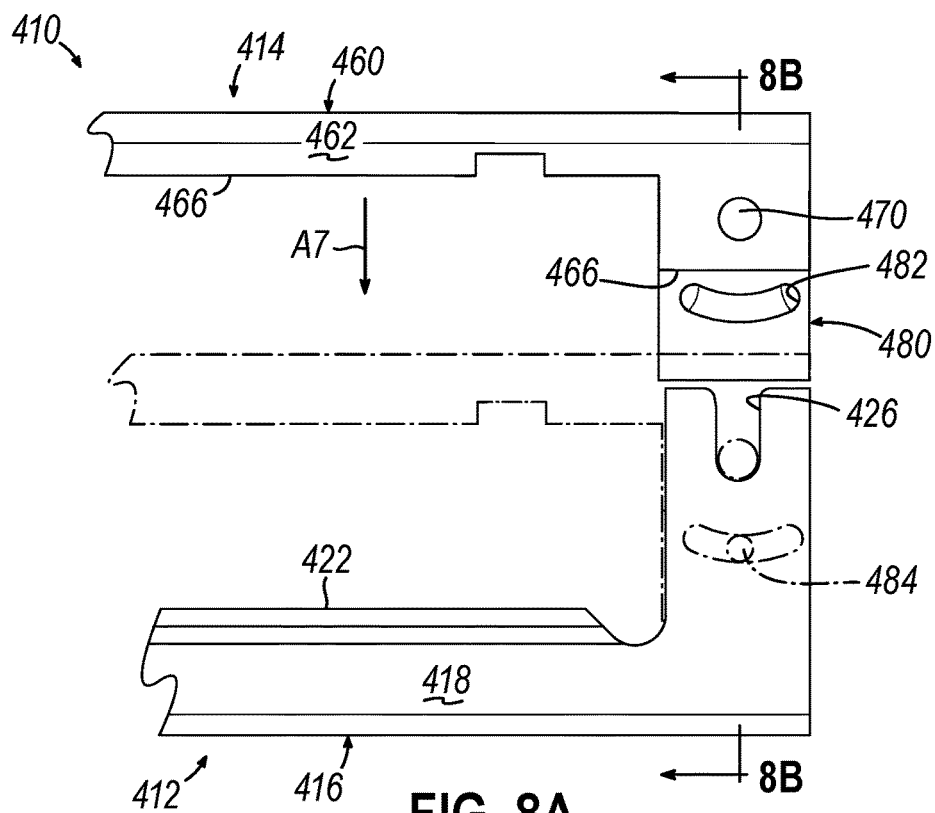
FIG. 8A depicts a side elevational view of a proximal end of another exemplary linear surgical stapler having an anvil insert with arched grooves and corresponding detents on the cartridge half, showing insertion of the detents into the grooves during linear approximation of the stapler halves for coupling the stapler halves at their proximal ends.
Figure 8B:
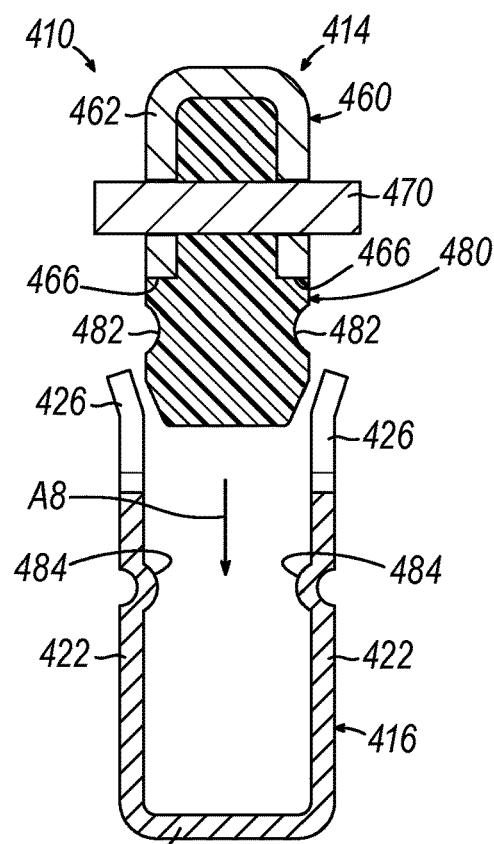
FIG. 8B depicts a cross sectional view of the proximal end of the linear surgical stapler of FIG. 8A, taken along section line 8B-8B in FIG. 8A, showing linear approximation of the stapler halves.

C. Exemplary Linear Cutter Separation Mechanism with Anvil Insert Having Arched Grooves and Corresponding Detents on Cartridge Half In some instances, it may be desirable to provide a surgical stapler separation mechanism which assists in guiding rotation of the stapler halves relative to each other. FIGS. 8A-8B show another exemplary surgical stapler (410) including a cartridge half (412) and an anvil half (414) that are configured in such a manner, and which are similar in structure and function to stapler (210) described above except as otherwise described below.

Cartridge half (412) includes an elongate cartridge channel (416) having a proximal frame portion (418) including a laterally opposed pair of upright side flanges (422), each including a notch (426) arranged at a proximal end thereof. Anvil half (414) includes an elongate anvil channel (460) having a proximal frame portion (462) including a laterally opposed pair of upright side flanges (466) that are configured to be received between cartridge channel side flanges (422) when anvil half (414) is coupled with cartridge half (412). A proximal pivot projection in the form of a round (e.g., circular) proximal pin (470) extends laterally through the proximal ends of anvil channel side flanges (466).

In the example shown, anvil half (414) further includes an anvil insert (480) extending downwardly from proximal anvil pin (470) between side flanges (466) and including a laterally opposed pair of arched grooves (482), each revolving partially about proximal anvil pin (470) between closed ends. Anvil insert (480) may be fixed against movement relative to anvil channel (460) and may be constructed of a plastic material, for example. Cartridge half (412) further includes a laterally opposed pair of detent members (484) extending laterally inwardly from side flanges (422) and vertically aligned with the respective notches (426).

Grooves (482) of anvil insert (480) are configured to releasably and movably capture detent members (484) with a friction fit or an interference fit when proximal anvil pin (470) is received within proximal notches (426) with anvil half (414) oriented relative to cartridge half (412) about proximal anvil pin (470) within a predetermined angular range, thereby coupling the proximal ends of stapler halves (412, 414). In this regard, the peripheral edges of grooves (482) may be configured to constrain movement of detent members (484) to a partial orbital path about proximal anvil pin (470), and to guide detent members (484) along such a path during rotation of anvil half (414) relative to cartridge half (412) about proximal anvil pin (470) between open and clamped states.

As best shown in FIG. 8B, grooves (482) and detent members (484) are sized relative to each other (e.g., in the lateral direction) to permit selective overriding of the interaction between detent members (484) and the peripheral edges of grooves (482) upon application of a threshold separating force applied between stapler halves (412, 414) to thereby withdraw detent members (484) from grooves (482). Likewise, anvil insert (480) and detent members (484) are sized relative to each other to permit selective overriding of any interaction between detent members (484) and a lower surface of anvil insert (480) upon application of a threshold approximating force applied between stapler halves (412, 414) to thereby insert detent members (484) into grooves (482), as indicated by seventh and eighth arrows (A7, A8) in FIG. 8A-8B, respectively.

Figure 9:
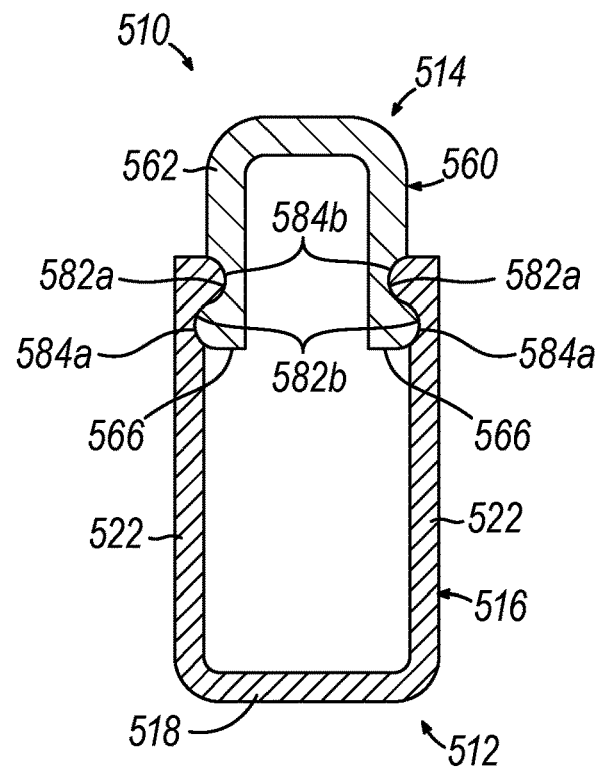
FIG. 9 depicts a cross sectional view of a proximal end of another exemplary linear surgical stapler having corresponding stamped indentations on the stapler halves for coupling the stapler halves at their proximal ends.

D. Exemplary Linear Cutter Separation Mechanism with Stamped Indentations on Anvil and Cartridge Halves In some instances, it may be desirable to provide a surgical stapler having a separation mechanism that is integrally formed with the channel members of the stapler halves. FIG. 9 shows another exemplary surgical stapler (510) including a cartridge half (512) and an anvil half (514) that are configured in such a manner, and which are similar in structure and function to stapler (210) described above except as otherwise described below.

Cartridge half (512) includes an elongate cartridge channel (516) having a proximal frame portion (518) including a laterally opposed pair of upright side flanges (522). Anvil half (514) includes an elongate anvil channel (560) having a proximal frame portion (562) including a laterally opposed pair of upright side flanges (566) that are configured to be received between cartridge channel side flanges (522) when anvil half (514) is coupled with cartridge half (512).

In the example shown, anvil half (514) further includes a first laterally opposed pair of grooves (582a) and a first laterally opposed pair of detent members (584a) extending laterally outwardly from side flanges (566). Likewise, cartridge half (512) includes a second laterally opposed pair of grooves (582b) and a second laterally opposed pair of detent members (584b) extending laterally inwardly from side flanges (522). Grooves (582a, 582b) and/or detent members (584a, 584b) may be arched in the longitudinal direction. In one example, grooves (582a, 582b) and/or detent members (584a, 584b) may be integrally formed together with the respective side flange(s) (522, 566) as a unitary piece(s). For example, grooves (582a), detent members (584a), and side flanges (566) may be stamped together on anvil channel (560), and grooves (582b), detent members (584b), and side flanges (522) may be stamped together on cartridge channel (516).

Grooves (582a, 582b) are configured to releasably and movably capture corresponding detent members (584a, 584b) with a friction fit or an interference fit when anvil half (514) is oriented relative to cartridge half (512) within a predetermined angular range, thereby coupling the proximal ends of stapler halves (512, 514). In this regard, the peripheral edges of grooves (582a, 582b) may be configured to constrain movement of detent members (584a, 584b) to a predetermined path, and to guide detent members (584a, 584b) along such a path during rotation of anvil half (514) relative to cartridge half (512) between open and clamped states.

While not shown, cartridge half (512) may include notches (not shown) arranged at proximal ends of side flanges (522), and anvil half (514) may include a proximal pivot projection in the form of a round (e.g., circular) proximal pin extending laterally through the proximal ends of anvil channel side flanges (566) for selective receipt by such notches.

Figure 10:
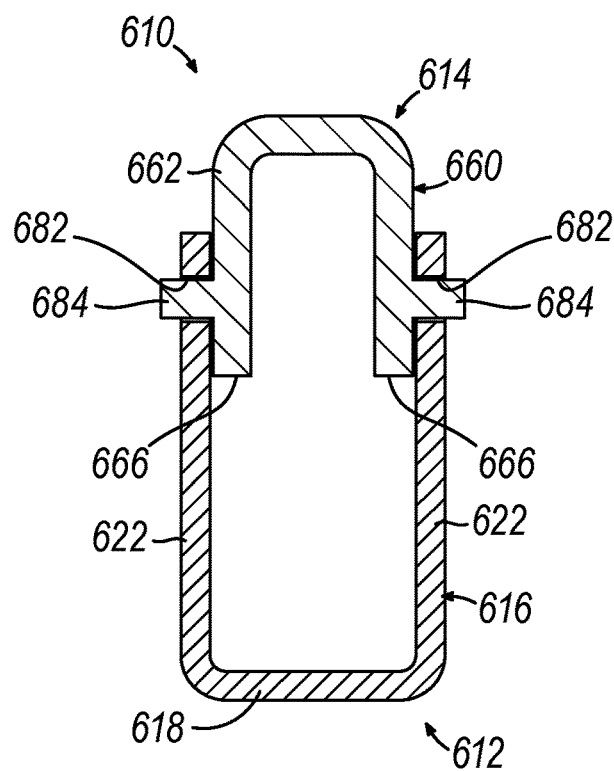
FIG. 10 depicts a cross sectional view of a proximal end of another exemplary linear surgical stapler having detents on the anvil half and corresponding arched grooves on the cartridge half for coupling the stapler halves.

E. Exemplary Linear Cutter Separation Mechanism with Detents on Anvil Half and Corresponding Arched Grooves on Cartridge Half In some instances, it may be desirable to provide a surgical stapler having a separation mechanism that is integrally formed with the channel members of the stapler halves different from that described above in connection to FIG. 9. FIG. 10 shows another exemplary surgical stapler (610) including a cartridge half (612) and an anvil half (614) that are configured in such a manner, and which are similar in structure and function to stapler (210) described above except as otherwise described below.

Cartridge half (612) includes an elongate cartridge channel (616) having a proximal frame portion (618) including a laterally opposed pair of upright side flanges (622). Anvil half (614) includes an elongate anvil channel (660) having a proximal frame portion (662) including a laterally opposed pair of upright side flanges (666) that are configured to be received between cartridge channel side flanges (622) when anvil half (614) is coupled with cartridge half (612).

In the example shown, cartridge half (612) further includes a laterally opposed pair of slots (682), and anvil half (614) includes a laterally opposed pair of detent members (684) extending laterally outwardly from side flanges (666). In one example, slots (682) may be arched in the longitudinal direction. In addition or alternatively, detent members (684) may be integrally formed together with the respective side flanges (666) as a unitary piece. For example, detent members (684) and side flanges (666) may be stamped together on anvil channel (660).

Slots (682) are configured to releasably and movably capture corresponding detent members (684) with a friction fit or an interference fit when anvil half (614) is oriented relative to cartridge half (612) within a predetermined angular range, thereby coupling the proximal ends of stapler halves (612, 614). In this regard, the peripheral edges of slots (682) may be configured to constrain movement of detent members (684) to a predetermined path, and to guide detent members (684) along such a path during rotation of anvil half (614) relative to cartridge half (612) between open and clamped states.

While not shown, cartridge half (612) may include notches (not shown) arranged at proximal ends of side flanges (622), and anvil half (614) may include a proximal pivot projection in the form of a round (e.g., circular) proximal pin extending laterally through the proximal ends of anvil channel side flanges (666) for selective receipt by such notches.

Figure 11:
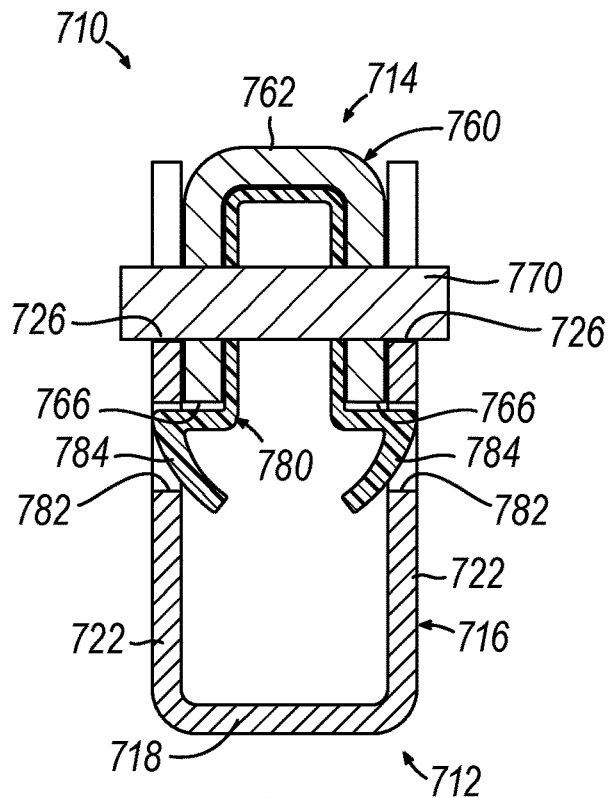
FIG. 11 depicts a cross sectional view of a proximal end of another exemplary linear surgical stapler having a metal leaf spring for coupling the stapler halves at their proximal ends.

F. Exemplary Linear Cutter Separation Mechanism with Metal Leaf Spring Insert In some instances, it may be desirable to provide a surgical stapler having a separation mechanism that is actuatable in the lateral direction. FIG. 11 shows another exemplary surgical stapler (710) including a cartridge half (712) and an anvil half (714) that are configured in such a manner, and which are similar in structure and function to stapler (710) described above except as otherwise described below.

Cartridge half (712) includes an elongate cartridge channel (716) having a proximal frame portion (718) including a laterally opposed pair of upright side flanges (722), each including a notch (726) arranged at a proximal end thereof. Anvil half (714) includes an elongate anvil channel (760) having a proximal frame portion (762) including a laterally opposed pair of upright side flanges (766) that are configured to be received between cartridge channel side flanges (722) when anvil half (714) is coupled with cartridge half (712). A proximal pivot projection in the form of a round (e.g., circular) proximal pin (770) extends laterally through the proximal ends of anvil channel side flanges (766).

In the example shown, anvil half (714) further includes an anvil insert (780) extending downwardly from proximal anvil pin (770) between side flanges (766), and cartridge half (712) further includes a laterally opposed pair of slots (782) vertically aligned with the respective notches (726). Anvil insert (780) may be constructed as a metal leaf spring, and includes a laterally opposed pair of spring arms (784) biased laterally outwardly from side flanges (766) to be releasably captured by slots (782) when proximal anvil pin (770) is received within proximal notches (726), thereby coupling the proximal ends of stapler halves (712, 714). Anvil insert (780) may be rotatable together with anvil channel (760) relative to cartridge channel (716) about proximal anvil pin (770), or alternatively may be rotatable together with cartridge channel (716) relative to anvil channel (760) about proximal anvil pin (770). In cases with the former configuration, slots (782) may be arched in the longitudinal direction to constrain movement of spring arms (784) to a partial orbital path about proximal anvil pin (770), and to guide spring arms (784) along such a path during rotation of anvil half (714) relative to cartridge half (712) about proximal anvil pin (770) between open and clamped states. In cases with the latter configuration, slots (782) may be sized to inhibit movement of spring arms (784) in the longitudinal direction.

As shown, slots (782) and spring arms (784) are sized relative to each other (e.g., in the lateral direction) to permit selective overriding of the interaction between spring arms (784) and the peripheral edges of slots (782) upon application of a threshold laterally-inward force applied to spring arms (784) to thereby withdraw spring arms (784) from slots (782). In one example, springs arms (784) may include camming surfaces configured to interact with upper surfaces of cartridge side flanges (722) to urge spring arms (784) laterally inwardly during coupling of stapler halves (712, 714).

G. Exemplary Linear Cutter Separation Mechanism with Molded Plastic Insert

Figure 12:
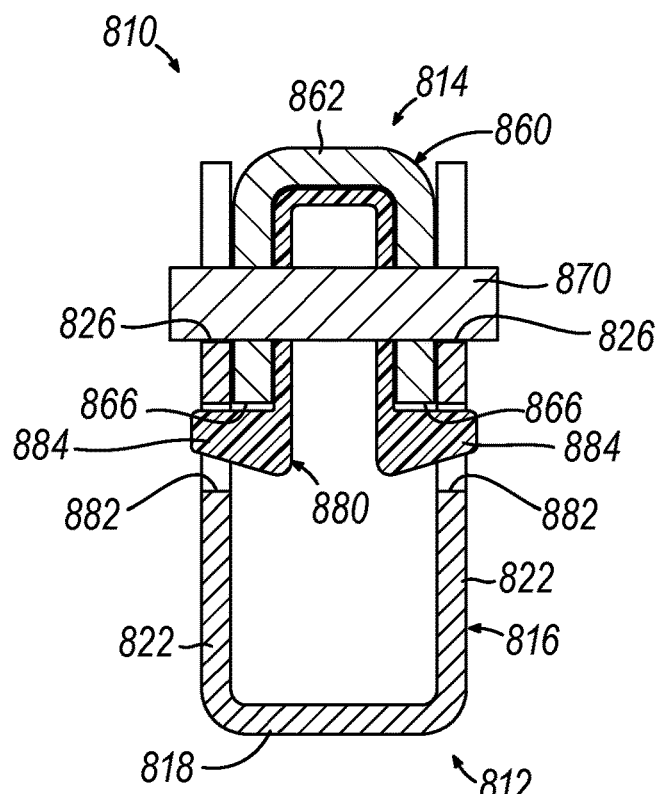
FIG. 12 depicts a cross sectional view of a proximal end of another exemplary linear surgical stapler having a plastic insert for coupling the stapler halves at their proximal ends.

In some instances, it may be desirable to provide a surgical stapler having a separation mechanism that is actuatable in the lateral direction different from that described above in connection to FIG. 11. FIG. 12 shows another exemplary surgical stapler (810) including a cartridge half (812) and an anvil half (814) that are configured in such a manner, and which are similar in structure and function to stapler (810) described above except as otherwise described below.

Cartridge half (812) includes an elongate cartridge channel (816) having a proximal frame portion (818) including a laterally opposed pair of upright side flanges (822), each including a notch (826) arranged at a proximal end thereof. Anvil half (814) includes an elongate anvil channel (860) having a proximal frame portion (862) including a laterally opposed pair of upright side flanges (866) that are configured to be received between cartridge channel side flanges (822) when anvil half (814) is coupled with cartridge half (812). A proximal pivot projection in the form of a round (e.g., circular) proximal pin (870) extends laterally through the proximal ends of anvil channel side flanges (866).

In the example shown, anvil half (814) further includes an anvil insert (880) extending downwardly from proximal anvil pin (870) between side flanges (866), and cartridge half (812) further includes a laterally opposed pair of slots (882) vertically aligned with the respective notches (826). Anvil insert (880) may be constructed of a plastic material, and includes a laterally opposed pair of resilient arms (884) biased laterally outwardly from side flanges (866) to be releasably captured by slots (882) when proximal anvil pin (870) is received within proximal notches (826), thereby coupling the proximal ends of stapler halves (812, 814). Anvil insert (880) may be rotatable together with anvil channel (860) relative to cartridge channel (816) about proximal anvil pin (870), or alternatively may be rotatable together with cartridge channel (816) relative to anvil channel (860) about proximal anvil pin (870). In cases with the former configuration, slots (882) may be arched in the longitudinal direction to constrain movement of resilient arms (884) to a partial orbital path about proximal anvil pin (870), and to guide resilient arms (884) along such a path during rotation of anvil half (814) relative to cartridge half (812) about proximal anvil pin (870) between open and clamped states. In cases with the latter configuration, slots (882) may be sized to inhibit movement of resilient arms (884) in the longitudinal direction.

As shown, slots (882) and resilient arms (884) are sized relative to each other (e.g., in the lateral direction) to permit selective overriding of the interaction between resilient arms (884) and the peripheral edges of slots (882) upon application of a threshold laterally-inward force applied to resilient arms (884) to thereby withdraw resilient arms (884) from slots (882). In one example, resilient arms (884) may include camming surfaces configured to interact with upper surfaces of cartridge side flanges (822) to urge resilient arms (884) laterally inwardly during coupling of stapler halves (812, 814).

Figure 13:
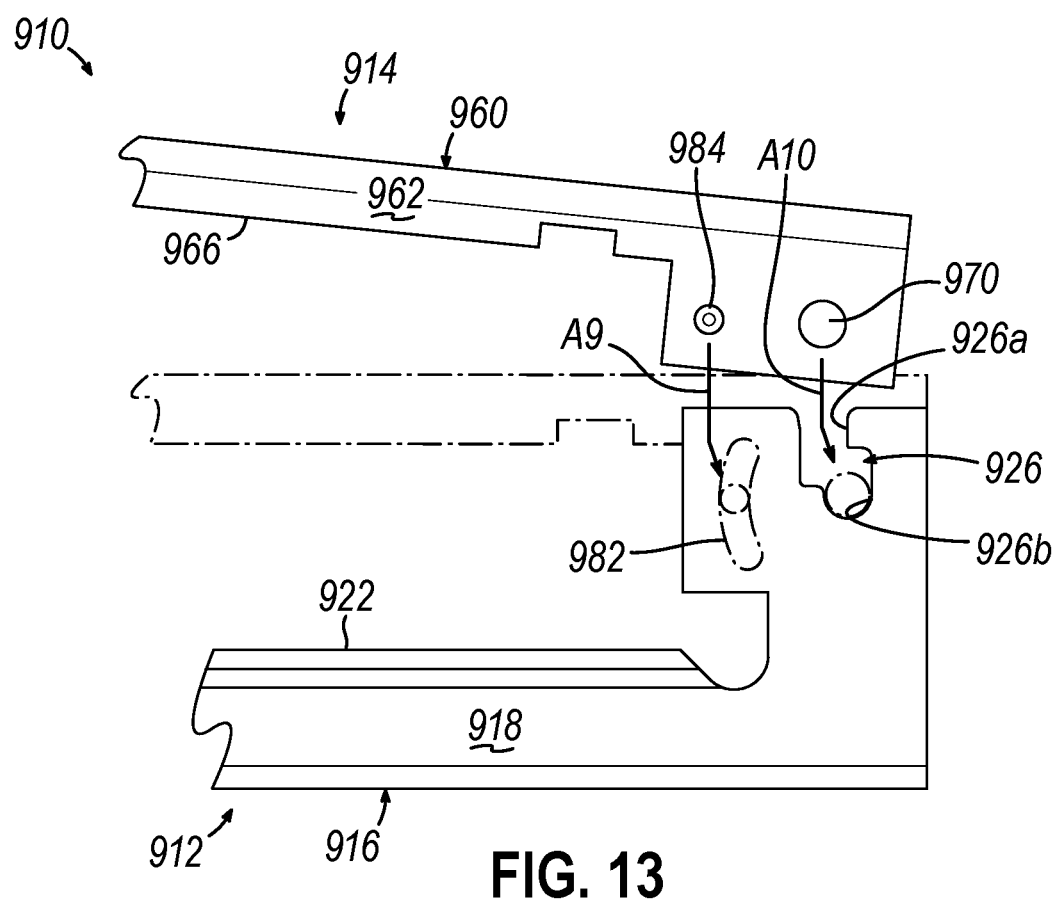
FIG. 13 depicts a side elevational view of a proximal end of another exemplary linear surgical stapler having a cartridge half with a stepped anvil pin receiving notch and arched grooves, and having an anvil half with corresponding detents, showing insertion of the detents into the grooves during linear approximation of the stapler halves for coupling the stapler halves at their proximal ends.

H. Exemplary Linear Cutter Separation Mechanism with Stepped Anvil Pin Receiving Notch on Cartridge Half In some instances, it may be desirable to provide a surgical stapler separation mechanism which assists in guiding rotation of the stapler halves relative to each other. FIG. 13 shows another exemplary surgical stapler (910) including a cartridge half (912) and an anvil half (914) that are configured in such a manner, and which are similar in structure and function to stapler (210) described above except as otherwise described below.

Cartridge half (912) includes an elongate cartridge channel (916) having a proximal frame portion (918) including a laterally opposed pair of upright side flanges (922), each including a notch (926) arranged at a proximal end thereof. Anvil half (914) includes an elongate anvil channel (960) having a proximal frame portion (962) including a laterally opposed pair of upright side flanges (966) that are configured to be received between cartridge channel side flanges (922) when anvil half (914) is coupled with cartridge half (912). A proximal pivot projection in the form of a round (e.g., circular) proximal pin (970) extends laterally through the proximal ends of anvil channel side flanges (966).

In the example shown, each notch (926) is stepped. More particularly, each notch (926) includes a first notch portion (926a) extending downwardly from an open end positioned on an upper surface of the respective side flange (922) to a second notch portion (926b) longitudinally offset from first notch portion (926a) and extending downwardly to a closed end for facilitating releasable coupling of stapler halves (912, 914). Also in the example shown, cartridge half (912) further includes at least one arched groove (982) revolving partially about the closed end of second notch portion (926b) between closed ends. Anvil half (914) further includes a laterally opposed pair of detent members (984) extending laterally outwardly from side flanges (966).

Groove (982) is configured to releasably and movably capture detent member (984) with a snap fit when proximal anvil pin (970) is positioned at the closed end of second notch portion (926b) with anvil half (914) oriented relative to cartridge half (912) about proximal anvil pin (970) within a predetermined angular range, thereby coupling the proximal ends of stapler halves (912, 914). In this regard, the peripheral edges of groove (982) may be configured to constrain movement of detent member (984) to a partial orbital path about proximal anvil pin (970), and to guide detent member (984) along such a path during rotation of anvil half (914) relative to cartridge half (912) about proximal anvil pin (970) between open and clamped states.

As shown, groove (982) and detent member (984) are sized relative to each other (e.g., in the lateral direction) to permit selective overriding of the interaction between detent member (984) and the peripheral edges of groove (982) upon application of a threshold separating force applied between stapler halves (912, 914) to thereby withdraw detent member (984) from groove (982). Likewise, cartridge side flanges (922) and detent member (984) are sized relative to each other to permit selective overriding of any interaction between detent member (984) and the upper surface of cartridge side flanges (922) upon application of a threshold approximating force applied between stapler halves (912, 914) to thereby insert detent member (984) into groove (982) while also positioning proximal anvil pin (970) at the closed end of second notch portion (926b), as indicated by ninth and tenth arrows (A9, A10), respectively, in FIG. 13.

Figure 14A:
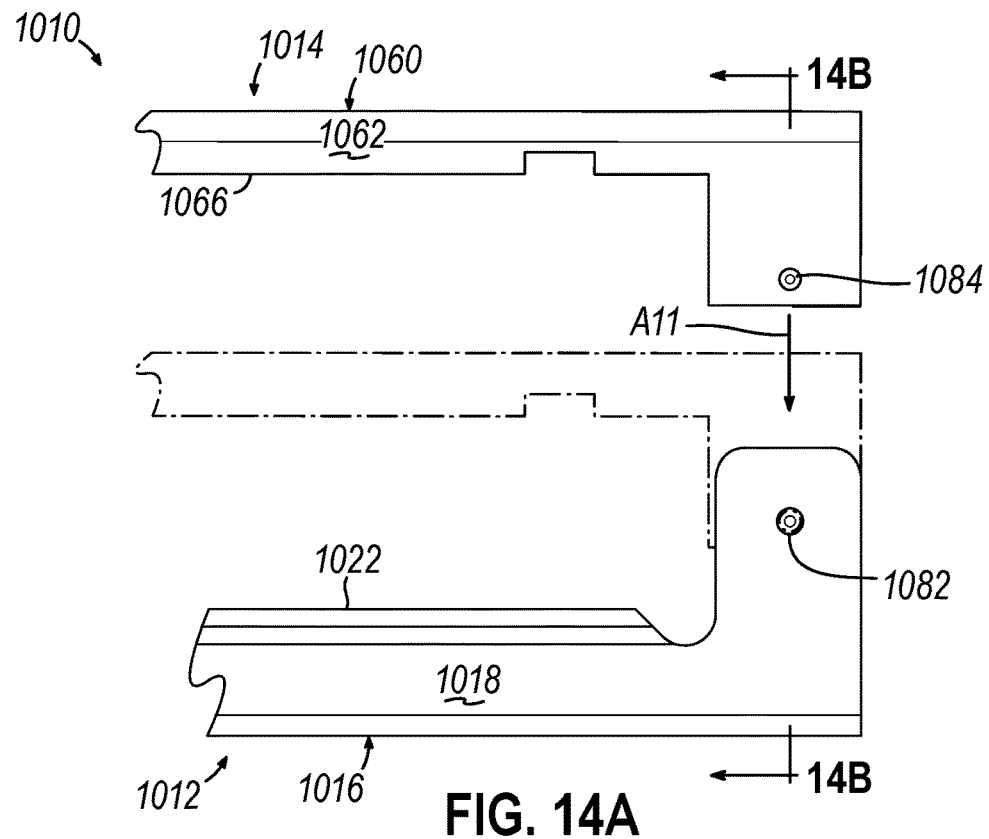
FIG. 14A depicts a side elevational view of a proximal end of another exemplary linear surgical stapler having corresponding proximal anvil detents and proximal cartridge indents, showing insertion of the detents into the indents during linear approximation of the stapler halves for coupling the stapler halves at their proximal ends.
Figure 14B:
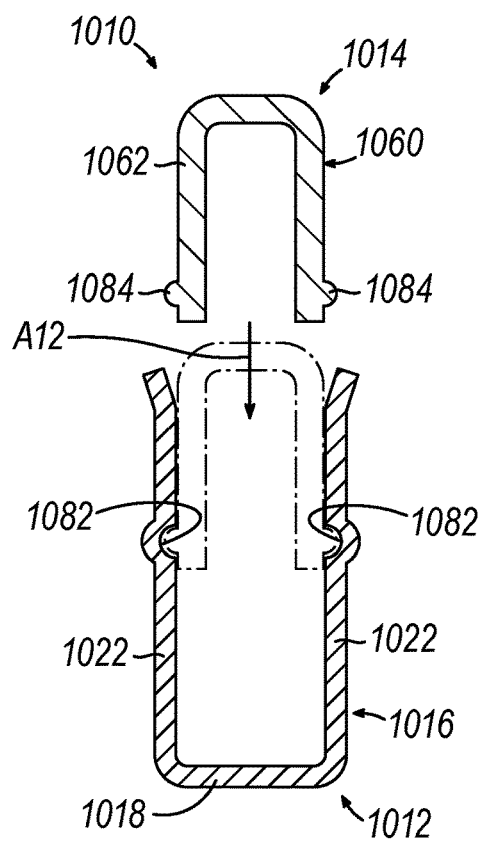
FIG. 14B depicts a cross sectional view of the proximal end of the linear surgical stapler of FIG. 14A, taken along section line 14B-14B in FIG. 14A, showing insertion of the detents into the indents during linear approximation of the stapler halves for coupling the stapler halves at their proximal ends.

I. Exemplary Linear Cutter Separation Mechanism with Proximal Anvil Detents and Corresponding Proximal Cartridge Indents In some instances, it may be desirable to provide a surgical stapler having a separation mechanism that allows an increased angular range of rotation between the stapler halves. FIGS. 14A-14B show another exemplary surgical stapler (1010) including a cartridge half (1012) and an anvil half (1014) that are configured in such a manner, and which are similar in structure and function to stapler (210) described above except as otherwise described below.

Cartridge half (1012) includes an elongate cartridge channel (1016) having a proximal frame portion (1018) including a laterally opposed pair of upright side flanges (1022). Anvil half (1014) includes an elongate anvil channel (1060) having a proximal frame portion (1062) including a laterally opposed pair of upright side flanges (1066) that are configured to be received between cartridge channel side flanges (1022) when anvil half (1014) is coupled with cartridge half (1012).

In the example shown, cartridge half (1012) further includes a laterally opposed pair of indent members (1082) positioned on side flanges (1022), and anvil half (1014) further includes a pair of proximal pivot projections in the form of laterally opposed detent members (1084) extending laterally outwardly from side flanges (1066). Indent members (1082) are configured to releasably and pivotably capture detent members (1084) with a friction fit or a snap fit such that indent members (1082) and detent members (1084) may collectively define a pivot axis of anvil half (1014) relative to cartridge half (1012). In one example, indent members (1082) and/or detent members (1084) may be integrally formed together with the respective side flanges (1022, 1066) as a unitary piece(s). For example, indent members (1082) and/or detent members (1084) may be coined on the respective side flanges (1022, 1066).

As shown, indent member (1082) and detent member (1084) are sized relative to each other (e.g., in the lateral direction) to permit selective overriding of the interaction between detent member (1084) and the peripheral edges of indent member (1082) upon application of a threshold separating force applied between stapler halves (1012, 1014) to thereby withdraw detent member (1084) from indent member (1082). Likewise, cartridge side flanges (1022) and detent member (1084) are sized relative to each other to permit selective overriding of any interaction between detent member (1084) and the upper surface of cartridge side flanges (1022) upon application of a threshold approximating force applied between stapler halves (1012, 1014) to thereby insert detent member (1084) into indent member (1082), as indicated by eleventh and twelfth arrows (A11, A12) in FIGS. 14A and 14B, respectively.

Figure 15A:
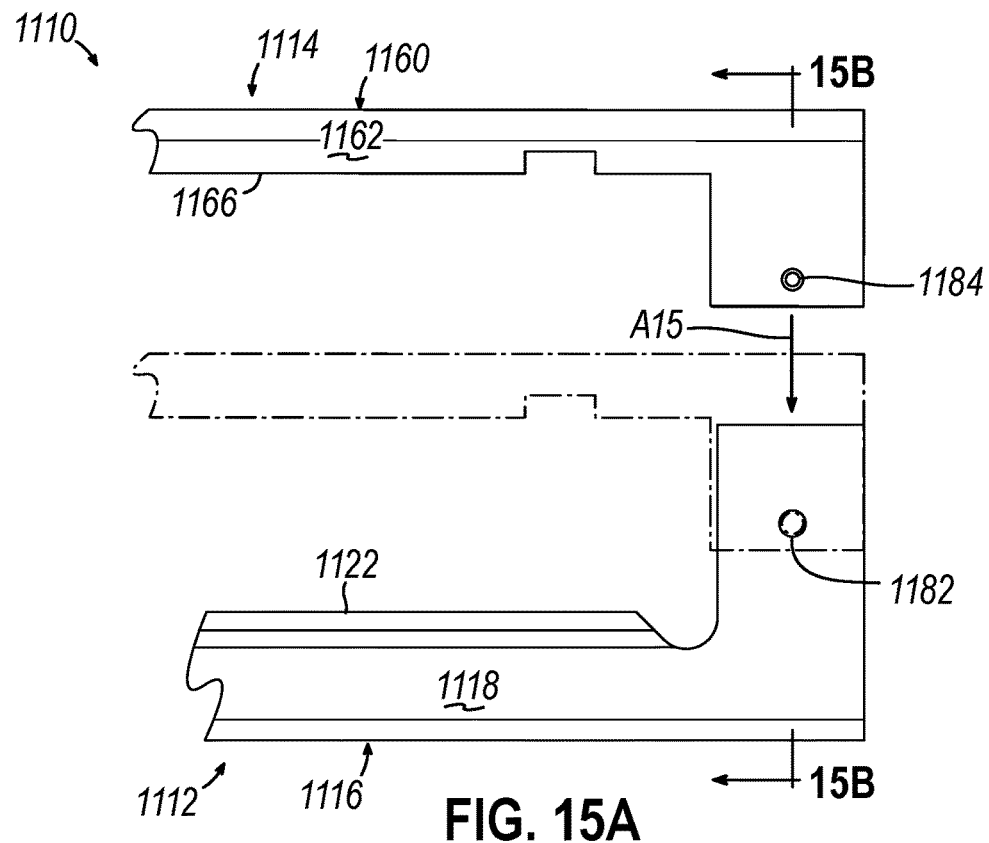
FIG. 15A depicts a side elevational view of a proximal end of another exemplary linear surgical stapler having a proximal anvil springbar and corresponding proximal cartridge bores, showing insertion of the springbar into the bores during linear approximation of the stapler halves for coupling the stapler halves at their proximal ends.
Figure 15B:
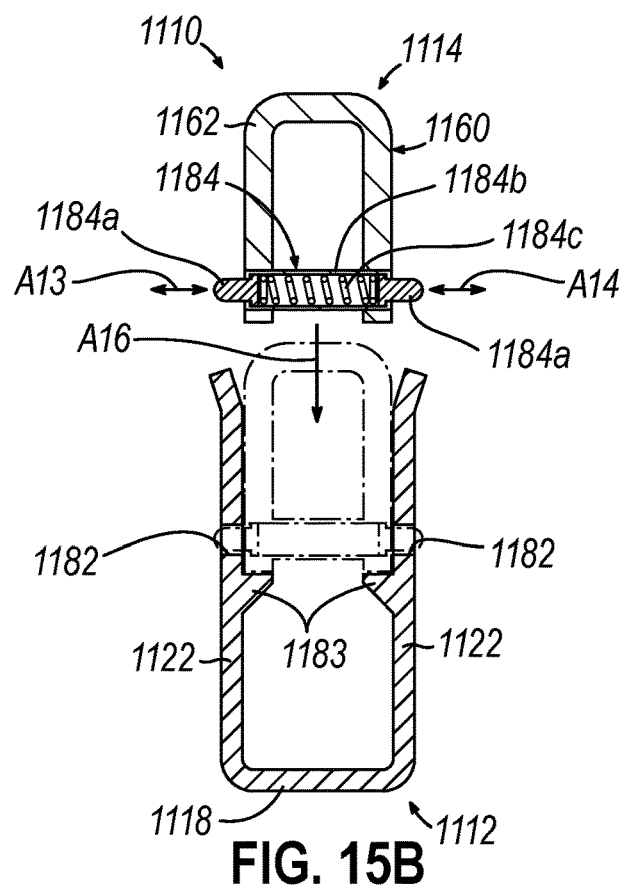
FIG. 15B depicts a cross sectional view of the proximal end of the linear surgical stapler of FIG. 15A, taken along section line 15B-15B in FIG. 15A, showing insertion of the springbar into the bores during linear approximation of the stapler halves for coupling the stapler halves at their proximal ends.

J. Exemplary Linear Cutter Separation Mechanism with Springbar-Type Proximal Anvil Pin In some instances, it may be desirable to provide a surgical stapler having a separation mechanism that allows an increased angular range of rotation between the stapler halves different from that described above in connection to FIGS. 14A-14B. FIGS. 15A-15B show another exemplary surgical stapler (1110) including a cartridge half (1112) and an anvil half (1114) that are configured in such a manner, and which are similar in structure and function to stapler (210) described above except as otherwise described below.

Cartridge half (1112) includes an elongate cartridge channel (1116) having a proximal frame portion (1118) including a laterally opposed pair of upright side flanges (1122). Anvil half (1114) includes an elongate anvil channel (1160) having a proximal frame portion (1162) including a laterally opposed pair of upright side flanges (1166) that are configured to be received between cartridge channel side flanges (1122) when anvil half (1114) is coupled with cartridge half (1112).

In the example shown, cartridge half (1112) further includes a laterally opposed pair of bores (1182) positioned on side flanges (1122) and a laterally opposed pair of support tabs (1183) extending laterally inwardly from side flanges (1122) and vertically aligned with bores (1182) for selectively supporting anvil half (1114) (e.g., when anvil half (1114) is in a clamped state). Anvil half (1114) further includes a proximal pivot projection in the form of a springbar (1184) including a laterally opposed pair of pins (1184a) biased laterally outwardly from a cylindrical tube (1184b) by a resilient member in the form of a compression spring (1184c). Pins (1184a) are further biased laterally outwardly from side flanges (1166) to be releasably and pivotably captured by bores (1182), thereby coupling the proximal ends of stapler halves (1112, 1114).

As shown, bores (1182) and springbar (1184) are sized relative to each other (e.g., in the lateral direction) to permit selective overriding of the interaction between pins (1184a) and the peripheral edges of bores (1182) upon application of a threshold laterally-inward force applied to pins (1184a) and/or upon application of a threshold separating (e.g., pulling or prying) force applied between stapler halves (1112, 1114) to thereby withdraw pins (1184a) from bores (1182), as indicated by thirteenth and fourteenth arrows (A13, A14) in FIG. 15B. In one example, upper surfaces of cartridge side flanges (1122) may include camming surfaces configured to interact with pins (1184a) to urge pins (1184a) laterally inwardly during coupling of stapler halves (1112, 1114), as indicated by fifteenth and sixteenth arrows (A15, A16) in FIGS. 15A and 15B, respectively.

In one example, anvil half (1114) may also include an anvil channel stop tab (not shown) projecting proximally from a proximal end of anvil channel (1160) and having a T-like shape defining a lateral width that increases proximally for engaging and pivoting relative to cartridge side flanges (1122) in a lever-fulcrum arrangement to assist in overcoming the laterally-outward biasing of pins (1184a) in response to rotation of anvil half (1114) away from cartridge half (1112) to a predetermined maximum orientation for decoupling of stapler halves (1112, 1114). Such an anvil channel stop tab may be configured in accordance with the teachings of U.S. patent application Ser. No. 16/165,587, incorporated by reference above.

Figure 16:
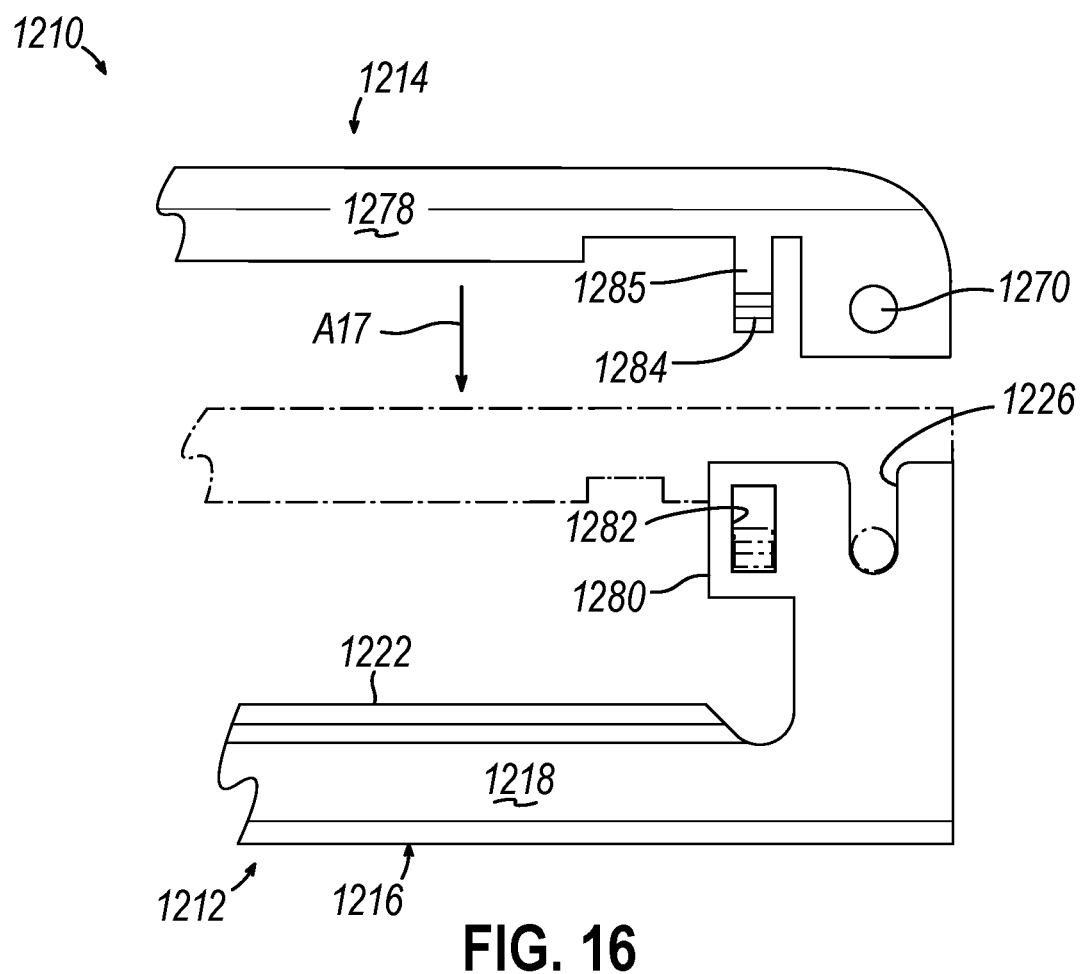
FIG. 16 depicts a side elevational view of a proximal end of another exemplary linear surgical stapler having an aperture positioned on the cartridge half and a corresponding detent positioned on the anvil shroud, showing insertion of the detent into the aperture during linear approximation of the stapler halves for coupling the stapler halves at their proximal ends.

K. Exemplary Linear Cutter Separation Mechanism with Tab on Anvil Shroud and Corresponding Aperture on Cartridge Half In some instances, it may be desirable to provide a surgical stapler having a separation mechanism with a portion thereof positioned on the anvil shroud. FIG. 16 shows another exemplary surgical stapler (1210) including a cartridge half (1212) and an anvil half (1214) that are configured in such a manner, and which are similar in structure and function to stapler (210) described above except as otherwise described below.

Cartridge half (1212) includes an elongate cartridge channel (1216) having a proximal frame portion (1218) including a laterally opposed pair of upright side flanges (1222), each including a notch (1226) arranged at a proximal end thereof. Anvil half (1214) includes an elongate anvil channel having a proximal frame portion including a laterally opposed pair of upright side flanges (not shown) that are configured to be received between cartridge channel side flanges (1222) when anvil half (1214) is coupled with cartridge half (1212). A proximal pivot projection in the form of a round (e.g., circular) proximal pin (1270) extends laterally through the proximal ends of the anvil channel side flanges. Additionally, an anvil shroud (1278) is affixed to and covers an outwardly facing side of the anvil channel.

In the example shown, cartridge half (1212) further includes at least one window frame (1280) defining an aperture (1282) and extending distally from a proximal portion of side flange (1222). Anvil half (1214) further includes at least one detent member (1284) configured to selectively engage window frame (1280) for facilitating releasable coupling of stapler halves (1212, 1214). Detent member (1284) of the present example is positioned on and extends laterally outwardly from a tab (1285) extending downwardly from anvil shroud (1278) such that detent member (284) is capable of extending laterally into aperture (1282). In one example, detent member (1284) and tab (1285) may be integrally formed together with anvil shroud (1278) as a unitary piece. Alternatively, detent member (1284) and tab (1285) may be separately formed apart from anvil shroud (1278) and coupled thereto, such as via welding or snapping.

As shown, aperture (1282) and detent member (1284) are sized relative to each other (e.g., in the lateral direction) to permit selective overriding of the interaction between detent member (1284) and the upper peripheral edge of aperture (1282) upon application of a threshold laterally-inward force applied to detent member (1284) and/or upon application of a threshold separating (e.g., pulling or prying) force applied between stapler halves (1212, 1214) to thereby withdraw detent member (1284) from aperture (1282). Likewise, window frame (1280) and detent member (1284) are sized relative to each other to permit selective overriding of any interaction between detent member (1284) and an upper surface of window frame (1280) upon application of a threshold approximating force applied between stapler halves (1212, 1214) to thereby insert detent member (1284) into aperture (1282) and couple stapler halves (1212, 1214)

to each other. In one example, detent member (1284) may include upper and/or lower camming surfaces configured to interact with the upper peripheral edge of aperture (1282) and/or the upper surface of window frame (1280) to urge detent member (1284) laterally inwardly during coupling and/or separation of stapler halves (1212, 1214), as indicated by seventeenth arrow (A17) in FIG. 16.

Figure 17A:
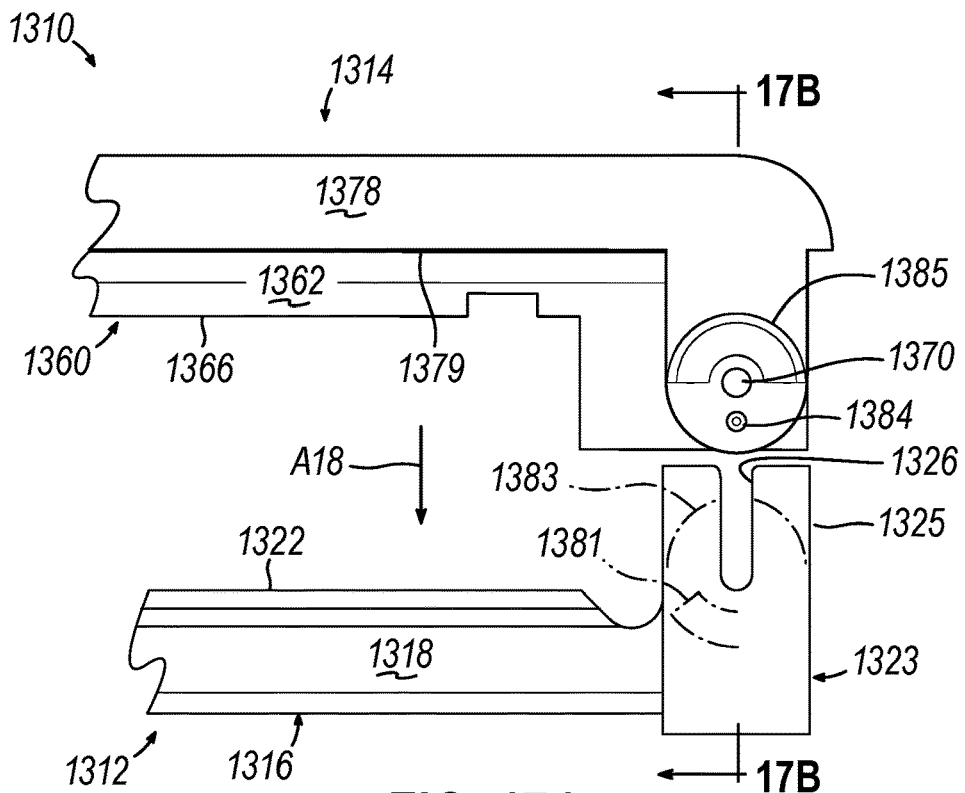
FIG. 17A depicts a side elevational view of a proximal end of another exemplary linear surgical stapler having corresponding arched surfaces on the stapler shrouds for coupling the stapler halves and corresponding camming separation features on the stapler shrouds for separating the stapler halves, showing linear approximation of the stapler halves.
Figure 17B:
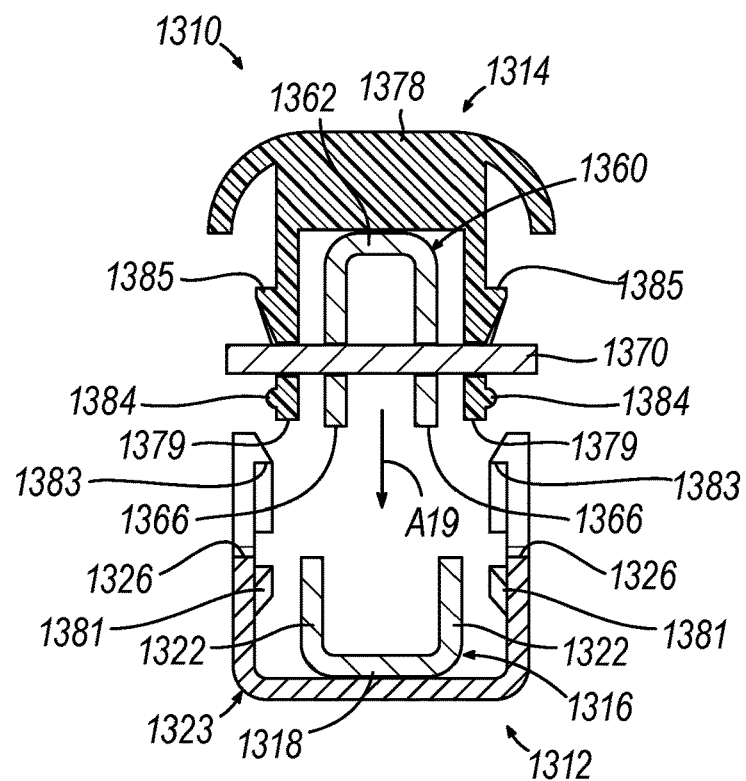
FIG. 17B depicts a cross sectional view of the proximal end of the linear surgical stapler of FIG. 17A, taken along section line 17B-17B in FIG. 17A, showing linear approximation of the stapler halves.

L. Exemplary Linear Cutter Separation Mechanism with Camming Separation Surfaces In some instances, it may be desirable to provide a surgical stapler having a separation mechanism with camming features on the cartridge and anvil shrouds. FIGS. 17A-17B show another exemplary surgical stapler (1310) including a cartridge half (1312) and an anvil half (1314) that are configured in such a manner, and which are similar in structure and function to stapler (210) described above except as otherwise described below.

Cartridge half (1312) includes an elongate cartridge channel (1316) having a proximal frame portion (1318) including a laterally opposed pair of upright side flanges (1322). Additionally, a proximal cartridge shroud (1323) is affixed to and covers a proximal outwardly facing side of cartridge channel (1316). Cartridge shroud (1323) includes a laterally opposed pair of upright side flanges (1325) each including a notch (1326). Anvil half (1314) includes an elongate anvil channel (1360) having a proximal frame portion (1362) including a laterally opposed pair of upright side flanges (1366) that are configured to be received between cartridge channel side flanges (1322) when anvil half (1314) is coupled with cartridge half (1312). A proximal pivot projection in the form of a round (e.g., circular) proximal pin (1370) extends laterally through the proximal ends of anvil channel side flanges (1366). Additionally, an anvil shroud (1378) is affixed to and covers an outwardly facing side of anvil channel (1360). Anvil shroud (1378) includes a laterally opposed pair of upright side flanges (1379), and proximal anvil pin (1370) extends laterally through the proximal ends of anvil shroud side flanges (1379).

In the example shown, cartridge half (1312) further includes a laterally opposed pair of arched cam ramps (1381) extending laterally inwardly from side flanges (1325) below closed ends of the respective notches (1326). More particularly, arched cam ramps (1381) each partially revolve about the closed end of the respective notch (1326), and taper or curve laterally inwardly from an origin on side flange (1325) generally vertically aligned with the respective notch (1326) to a laterally inwardmost terminus slightly below and distal to the respective notch (1326). Cartridge half (1312) also includes a laterally opposed pair of arched shoulders (1383) extending laterally inwardly from side flanges (1325) above closed ends of the respective notches (1326) and intersected by the respective notches (1326). More particularly, arched shoulders (1383) each partially revolve about the closed end of the respective notch (1326) between proximal and distal ends generally horizontally aligned with the closed end of the respective notch (1326).

Also in the example shown, anvil half (1314) further includes a laterally opposed pair of detent members (1384) extending laterally outwardly from side flanges (1379) below proximal anvil pin (1370). Anvil half (1314) also includes a laterally opposed pair of arched ledges (1385) extending laterally outwardly from side flanges (1379) above proximal anvil pin (1370). More particularly, arched ledges (1385) each partially revolve about proximal anvil pin (1370) between proximal and distal ends generally horizontally aligned with proximal anvil pin (1370).

As best shown in FIG. 17B, arched shoulders (1383) are configured to releasably and movably confront arched ledges (1385) when proximal anvil pin (1370) is received within proximal notches (1326) with anvil half (1314) oriented relative to cartridge half (1312) about proximal anvil pin (1370) within a predetermined angular range, thereby coupling the proximal ends of stapler halves (1312, 1314). More particularly, arched shoulders (1383) may be configured to constrain movement of arched ledges (1385) to a partial orbital path about proximal anvil pin (1370), and to guide arched ledges (1385) along such a path during rotation of anvil half (1314) relative to cartridge half (1312) about proximal anvil pin (1370) within the predetermined angular range. In this regard, arched cam ramps (1381) may be configured to selectively urge detent members (1384) laterally inwardly to at least partially define one or more limits of the predetermined angular range. For example, detent members (1384) may each be configured to ride against the respective arched cam ramp (1381) between its origin and laterally inwardmost terminus and to be urged laterally inwardly thereby. In this manner, as detent members (1384) approach the respective laterally inwardmost termini, arched cam ramps (1381) may be configured to urge detent members (1384) sufficiently laterally inwardly to cause arched ledges (1385) to deflect laterally inwardly relative to and disengage arched shoulders (1383) in response to rotation of anvil half (1314) away from cartridge half (1312) to a predetermined maximum orientation for decoupling of stapler halves (1312, 1314). In one example, arched shoulders (1383) and arched ledges (1385) may include camming surfaces configured to interact with each other to urge arched ledges (1385) laterally inwardly during coupling of stapler halves (1312, 1314), as indicated by eighteenth and nineteenth arrows (A18, A19) in FIGS. 17A and 17B, respectively.

Figure 18:
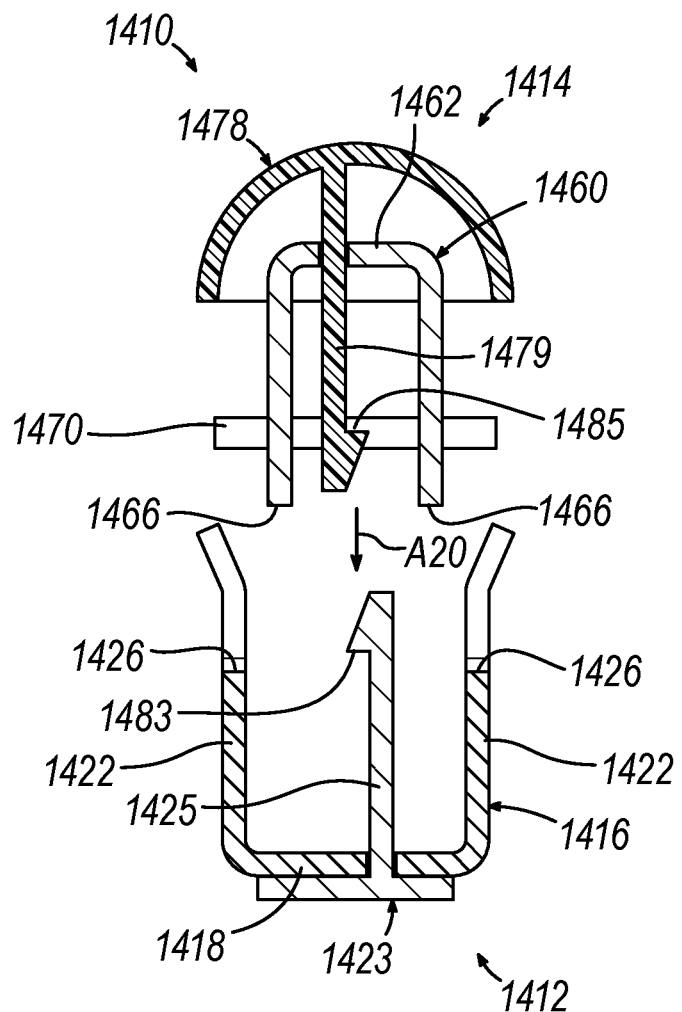
FIG. 18 depicts a cross sectional view of a proximal end of another exemplary linear surgical stapler having corresponding mating surfaces on the stapler shrouds for coupling the stapler halves, showing linear approximation of the stapler halves.

M. Exemplary Linear Cutter Separation Mechanism with Central Tabs on Anvil and Cartridge Halves In some instances, it may be desirable to provide a surgical stapler having a separation mechanism with portions thereof positioned on the cartridge and anvil shrouds different from that described above in connection to FIGS. 17A-17B. FIG. 18 shows another exemplary surgical stapler (1410) including a cartridge half (1412) and an anvil half (1414) that are configured in such a manner, and which are similar in structure and function to stapler (210) described above except as otherwise described below.

Cartridge half (1412) includes an elongate cartridge channel (1416) having a proximal frame portion (1418) including a laterally opposed pair of upright side flanges (1422) each including a notch (1426). Additionally, a proximal cartridge shroud (1423) is affixed to and covers at least a proximal downwardly facing side of cartridge channel (1416). Cartridge shroud (1423) includes a generally laterally centered upright flange (1425). Anvil half (1414) includes an elongate anvil channel (1460) having a proximal frame portion (1462) including a laterally opposed pair of upright side flanges (1466) that are configured to be received between cartridge channel side flanges (1422) when anvil half (1414) is coupled with cartridge half (1412). A proximal pivot projection in the form of a round (e.g., circular) proximal pin (1470) extends laterally through the proximal ends of anvil channel side flanges (1466). Additionally, an anvil shroud (1478) is affixed to and covers at least an upwardly facing side of anvil channel (1460). Anvil shroud (1478) includes a generally laterally centered upright flange (1479).

In the example shown, cartridge half (1412) further includes a shoulder (1483) extending laterally (e.g., leftward) from flange (1425), and anvil half (1414) further includes a ledge (1485) extending laterally (e.g., rightward) from flange (1479). Shoulder (1483) may be configured to releasably and movably confront ledge (1485) when proximal anvil pin (1470) is received within proximal notches (1426) with anvil half (1414) oriented relative to cartridge half (1412) about proximal anvil pin (1470) within a predetermined angular range, thereby coupling the proximal ends of stapler halves (1412, 1414). In one example, shoulder (1483) and/or ledge (1485) may be angled and/or arched in a manner(s) similar to that described above in connection to FIGS. 17A-17B. In one example, shoulder (1483) and ledge (1485) may include camming surfaces configured to interact with each other to urge ledge (1485) laterally outwardly during coupling of stapler halves (1412, 1414), as indicated by twentieth arrow (A20) in FIG. 18.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical stapler comprising: (a) a first half comprising: (i) a first elongate member, and (ii) a surface having a plurality of staple forming pockets; (b) a second half configured to releasably couple with the first half, wherein the second half comprises: (i) a second elongate member having a distal portion operable to deploy staples toward the first half, wherein the first and second elongate members are configured to be pivotable relative to each other about a pivot axis when the first half and the second half are releasably coupled together; (c) a latching member operable to selectively clamp the first half against the second half to thereby define a clamped state of the surgical stapler; (d) a detent member extending laterally relative to a longitudinal axis of the surgical stapler from one of the first half or the second half toward the other of the first half or the second half; and (e) a shoulder member positioned on the other of the first half or the second half, wherein the shoulder member is configured to selectively engage the detent member in response to rotation of the first elongate member away from the second elongate member about the pivot axis to an open state in which the first and second elongate members assume a predetermined maximum angular orientation relative to one another and remain releasably coupled together at their proximal ends.

Example 2

The surgical stapler of Example 1, wherein the shoulder member is defined by a peripheral edge of an aperture positioned on the other of the first half or the second half.

Example 3

The surgical stapler of Example 2, wherein the aperture is configured to capture the detent member such that the detent member is movable within the aperture when the first elongate member is angularly oriented relative to the second elongate member about the pivot axis within a predetermined angular range, wherein a first end of the predetermined angular range corresponds to the clamped state and a second end of the predetermined angular range is defined by the predetermined maximum angular orientation.

Example 4

The surgical stapler of any of the preceding Examples, wherein the detent member extends laterally outwardly from the first half, wherein the shoulder member is positioned on the second half.

Example 5

The surgical stapler of Example 4, wherein the detent member extends laterally outwardly from the first elongate member.

Example 6

The surgical stapler of Example 5, wherein the detent member is integrally formed with the first elongate member as a unitary piece.

Example 7

The surgical stapler of any one or more of Examples 1 through 3, wherein the detent member extends laterally inwardly from the second half, wherein the shoulder member is positioned on the first half.

Example 8

The surgical stapler of any of the preceding Examples, wherein the detent member is positioned distally relative to the pivot axis.

Example 9

The surgical stapler of any of the preceding Examples, wherein the shoulder member is positioned distally relative to the pivot axis.

Example 10

The surgical stapler of any of the preceding Examples, wherein the detent member includes a laterally opposed pair of detent members, wherein the shoulder member includes a laterally opposed pair of shoulder members.

Example 11

The surgical stapler of any of the preceding Examples, wherein the detent member and the shoulder member are laterally sized relative to each other to permit selective disengagement of the detent member from the shoulder member in response to application of a threshold force applied between the first half and the second half to thereby allow selective coupling and separating of the first half and the second half.

Example 12

The surgical stapler of Example 11, wherein the detent member and the shoulder member are laterally sized relative to each other to permit selective disengagement of the detent member from the shoulder member in response to application of a threshold rotational force applied between the first half and the second half about the pivot axis.

Example 13

The surgical stapler of any one or more of Examples 11 through 12, wherein the detent member and the shoulder member are laterally sized relative to each other to permit selective disengagement of the detent member from the shoulder member in response to application of a threshold linear force applied between the first half and the second half while the first half and the second half are parallel with each other.

Example 14

The surgical stapler of any of the preceding Examples, wherein the pivot axis is defined by a pin.

Example 15

The surgical stapler of any of the preceding Examples, wherein the distal portion of the second elongate member is configured to receive a staple cartridge.

Example 16

A surgical stapler comprising: (a) a first half comprising: (i) a first elongate member, (ii) a surface having a plurality of staple forming pockets, (iii) a distal latch projection, and (iv) a proximal pivot projection; (b) a second half configured to releasably couple with the first half, wherein the second half comprises: (i) a second elongate member having a distal portion operable to deploy staples toward the first half and at least one proximal notch configured to pivotably receive the proximal pivot projection of the first half, and (ii) a latching lever pivotably coupled to the second elongate member and configured to selectively engage the distal latch projection for clamping the first half against the second half to thereby define a clamped state of the surgical stapler; (c) a detent member extending laterally from one of the first half or the second half toward the other of the first half or the second half; and (d) an aperture positioned on the other of the first half or the second half and configured to capture the detent member such that the detent member is movable within the aperture when the first half is angularly oriented relative to the second half about the proximal pivot projection within a predetermined angular range, wherein a first end of the predetermined angular range corresponds to an open state in which the first and second elongate members assume a predetermined maximum angular orientation relative to one another and remain releasably coupled together at their proximal ends.

Example 17

The surgical stapler of Example 16, wherein the detent member extends laterally outwardly from the first half, wherein the aperture is positioned on the second half.

Example 18

The surgical stapler of Example 17, wherein the aperture includes an upper peripheral edge configured to selectively engage the detent member in response to rotation of the first half relative to the second half about the proximal pivot projection to the second end of the predetermined angular range to thereby define the open state of the surgical stapler.

Example 19

The surgical stapler of Example 18, wherein the detent member and the upper peripheral edge of the aperture are laterally sized relative to each other to permit selective disengagement of the detent member from the upper peripheral edge of the aperture in response to application of a threshold force applied between the first half and the second half to thereby allow selective separating of the first half and the second half.

Example 20

A surgical stapler comprising: (a) a first half comprising: (i) a first elongate member, (ii) a surface having a plurality of staple forming pockets, (iii) a distal latch projection, (iv) a proximal pivot projection, and (v) a detent member extending laterally outwardly from the first elongate member; and (b) a second half configured to releasably couple with the first half, wherein the second half comprises: (i) a second elongate member having a distal portion operable to deploy staples toward the first half and at least one proximal notch configured to pivotably receive the proximal pivot projection of the first half, (ii) a latching lever pivotably coupled to the second elongate member and configured to selectively engage the distal latch projection for clamping the first half against the second half to thereby define a clamped state of the surgical stapler, and (iii) a shoulder member configured to selectively engage the detent member in response to rotation of the first half away from the second half about the proximal pivot projection to an open state in which the first and second elongate members assume a predetermined maximum angular orientation relative to one another and remain releasably coupled together at their proximal ends.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Further, any one or more of the teachings, expressions, embodiments, examples, etc. described herein may be combined with any one or more of the teachings, expressions, embodiments, examples, etc. described in U.S. Pat. No. 10,631,866, entitled "Release Mechanism for Linear Surgical Stapler," issued on Apr. 28, 2020; U.S. Pub. No. 2019/0239882, entitled "Lockout Assembly for Linear Surgical Stapler," published on Aug. 8, 2019; U.S. Pub. No. 2019/0239886, entitled "Features to Align and Close Linear Surgical Stapler", published on Aug. 8, 2019; U.S. Pub. No. 2019/0239883, entitled "Releasable Coupling Features for Proximal Portions of Linear Surgical Stapler," published on Aug. 8, 2019; U.S. Pub. No. 2019/0239884, entitled "Firing Lever Assembly for Linear Surgical Stapler," published on Aug. 8, 2019; U.S. Pub. No. 2019/0239885, entitled "Clamping Mechanism for Linear Surgical Stapler," published on Aug. 8, 2019; U.S. Pub. No. 2020/0046350, entitled "Firing System for Linear Surgical Stapler," published on Feb. 13, 2020; U.S. Pub. No. 2020/0046353, entitled "Clamping Assembly for Linear Surgical Stapler," published on Feb. 13, 2020; U.S. Pub. No. 2020/0113561, entitled "Anvil Assembly for Linear Surgical Stapler," published on Apr. 16, 2020; U.S. Pub. No. 2020/0113562, entitled "Closure Assembly for Linear Surgical Stapler," published on Apr. 16, 2020; and/or U.S. Pub. No. 2020/0046351, entitled "Decoupling Mechanism for Linear Surgical Stapler," published on Feb. 13, 2020. The disclosure of each of these applications is incorporated by reference herein.

Further, any one or more of the teachings, expressions, embodiments, examples, etc. described herein may be combined with any one or more of the teachings, expressions, embodiments, examples, etc. described in U.S. application. Ser. No. 16/886,920, entitled "Pin Trap Mechanism for Surgical Linear Cutter," filed on May 29, 2020; and/or U.S. application Ser. No. 16/886,924, entitled "Separation Mechanism for Surgical Linear Cutter," filed on May 29,2020. The disclosure of each of these applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. A surgical stapler comprising:
   (a) a first half comprising:
      (i) a first elongate member, and
      (ii) a surface having a plurality of staple forming pockets;
   (b) a second half configured to releasably couple with the first half, wherein the second half comprises:
      (i) a second elongate member having a distal portion operable to deploy staples toward the first half, wherein the first and second elongate members are configured to be pivotable relative to each other about a pivot axis when the first half and the second half are releasably coupled together;
   (c) a latching member operable to selectively clamp the first half against the second half to thereby define a clamped state of the surgical stapler;
   (d) a detent member extending laterally relative to a longitudinal axis of the surgical stapler from one of the first half or the second half toward the other of the first half or the second half; and
   (e) a shoulder member positioned on the other of the first half or the second half, wherein the shoulder member is configured to selectively engage the detent member in response to rotation of the first elongate member away from the second elongate member about the pivot axis to an open state in which the first and second elongate members assume a predetermined maximum angular orientation relative to one another and remain releasably coupled together at their proximal ends.

2. The surgical stapler of claim 1, wherein the shoulder member is defined by a peripheral edge of an aperture positioned on the other of the first half or the second half.

3. The surgical stapler of claim 2, wherein the aperture is configured to capture the detent member such that the detent member is movable within the aperture when the first elongate member is angularly oriented relative to the second elongate member about the pivot axis within a predetermined angular range, wherein a first end of the predetermined angular range corresponds to the clamped state and a second end of the predetermined angular range is defined by the predetermined maximum angular orientation.

4. The surgical stapler of claim 1, wherein the detent member extends laterally outwardly from the first half, wherein the shoulder member is positioned on the second half.

5. The surgical stapler of claim 4, wherein the detent member extends laterally outwardly from the first elongate member.

6. The surgical stapler of claim 5, wherein the detent member is integrally formed with the first elongate member as a unitary piece.

7. The surgical stapler of claim 1, wherein the detent member extends laterally inwardly from the second half, wherein the shoulder member is positioned on the first half.

8. The surgical stapler of claim 1, wherein the detent member is positioned distally relative to the pivot axis.

9. The surgical stapler of claim 1, wherein the shoulder member is positioned distally relative to the pivot axis.

10. The surgical stapler of claim 1, wherein the detent member includes a laterally opposed pair of detent members, wherein the shoulder member includes a laterally opposed pair of shoulder members.

11. The surgical stapler of claim 1, wherein the detent member and the shoulder member are laterally sized relative to each other to permit selective disengagement of the detent member from the shoulder member in response to application of a threshold force applied between the first half and the second half to thereby allow selective coupling and separating of the first half and the second half.

12. The surgical stapler of claim 11, wherein the detent member and the shoulder member are laterally sized relative to each other to permit selective disengagement of the detent member from the shoulder member in response to application of a threshold rotational force applied between the first half and the second half about the pivot axis.

13. The surgical stapler of claim 11, wherein the detent member and the shoulder member are laterally sized relative to each other to permit selective disengagement of the detent member from the shoulder member in response to application of a threshold linear force applied between the first half and the second half while the first half and the second half are parallel with each other.

14. The surgical stapler of claim 1, wherein the pivot axis is defined by a pin.

15. The surgical stapler of claim 1, wherein the distal portion of the second elongate member is configured to receive a staple cartridge.

16. A surgical stapler comprising:
(a) a first half comprising:
  (i) a first elongate member,
  (ii) a surface having a plurality of staple forming pockets,
  (iii) a distal latch projection, and
  (iv) a proximal pivot projection;
(b) a second half configured to releasably couple with the first half, wherein the second half comprises:
  (i) a second elongate member having a distal portion operable to deploy staples toward the first half and at least one proximal notch configured to pivotably receive the proximal pivot projection of the first half, and
  (ii) a latching lever pivotably coupled to the second elongate member and configured to selectively engage the distal latch projection for clamping the first half against the second half to thereby define a clamped state of the surgical stapler;
(c) a detent member extending laterally from one of the first half or the second half toward the other of the first half or the second half; and
(d) an aperture positioned on the other of the first half or the second half and configured to capture the detent member such that the detent member is movable within the aperture when the first half is angularly oriented relative to the second half about the proximal pivot projection within a predetermined angular range, wherein a first end of the predetermined angular range corresponds to the clamped state and a second end of the predetermined angular range corresponds to an open state in which the first and second elongate members assume a predetermined maximum angular orientation relative to one another and remain releasably coupled together at their proximal ends.

17. The surgical stapler of claim 16, wherein the detent member extends laterally outwardly from the first half, wherein the aperture is positioned on the second half.

18. The surgical stapler of claim 17, wherein the aperture includes an upper peripheral edge configured to selectively engage the detent member in response to rotation of the first half relative to the second half about the proximal pivot projection to the second end of the predetermined angular range to thereby define the open state of the surgical stapler.

19. The surgical stapler of claim 18, wherein the detent member and the upper peripheral edge of the aperture are laterally sized relative to each other to permit selective disengagement of the detent member from the upper peripheral edge of the aperture in response to application of a threshold force applied between the first half and the second half to thereby allow selective separating of the first half and the second half.

20. A surgical stapler comprising:
(a) a first half comprising:
  (i) a first elongate member,
  (ii) a surface having a plurality of staple forming pockets,
  (iii) a distal latch projection,
  (iv) a proximal pivot projection, and
  (v) a detent member extending laterally outwardly from the first elongate member; and
(b) a second half configured to releasably couple with the first half, wherein the second half comprises:
  (i) a second elongate member having a distal portion operable to deploy staples toward the first half and at least one proximal notch configured to pivotably receive the proximal pivot projection of the first half,
  (ii) a latching lever pivotably coupled to the second elongate member and configured to selectively engage the distal latch projection for clamping the first half against the second half to thereby define a clamped state of the surgical stapler, and
  (iii) a shoulder member configured to selectively engage the detent member in response to rotation of the first half away from the second half about the proximal pivot projection to an open state in which the first and second elongate members assume a predetermined maximum angular orientation relative to one another and remain releasably coupled together at their proximal ends.

* * * * *